United States Patent
Kii et al.

(10) Patent No.: US 11,222,423 B2
(45) Date of Patent: Jan. 11, 2022

(54) EVALUATION DEVICE, OBSERVATION DEVICE, AND PROGRAM FOR IDENTIFYING CELL DIFFERENTIATION

(71) Applicants: NIKON CORPORATION, Tokyo (JP); NATL INST OF BIOMEDICAL INNOV, HEALTH & NUTRITION, Ibaraki (JP)

(72) Inventors: Hiroaki Kii, Kawasaki (JP); Yasujiro Kiyota, Tokyo (JP); Takayuki Uozumi, Tokyo (JP); Miho Furue, Osaka (JP); Mika Suga, Osaka (JP)

(73) Assignees: Nikon Corporation, Tokyo (JP); National Institutes Of Biomedical Innovation, Health And Nutrition, Osaka (JP)

( * ) Notice: Subject to any disclaimer, the term of this patent is extended or adjusted under 35 U.S.C. 154(b) by 660 days.

(21) Appl. No.: 16/125,064

(22) Filed: Sep. 7, 2018

(65) Prior Publication Data
US 2019/0087956 A1 Mar. 21, 2019

Related U.S. Application Data

(63) Continuation of application No. PCT/JP2016/057806, filed on Mar. 11, 2016.

(51) Int. Cl.
*G06K 9/00* (2006.01)
*G06T 7/00* (2017.01)
(Continued)

(52) U.S. Cl.
CPC .............. *G06T 7/0014* (2013.01); *C12M 1/00* (2013.01); *C12M 41/48* (2013.01); *C12Q 1/68* (2013.01);
(Continued)

(58) Field of Classification Search
CPC . G06T 2207/10056; G06T 2207/30024; G06T 7/0014; G06T 7/0012; G06T 7/97; G06K 9/00127; G06K 9/00134
See application file for complete search history.

(56) References Cited

U.S. PATENT DOCUMENTS

2002/0164063 A1 * 11/2002 Heckman .............. G06T 7/0012
382/133
2003/0103662 A1 6/2003 Finkbeiner
(Continued)

FOREIGN PATENT DOCUMENTS

EP 2551343 A1 1/2013
JP 2007/195533 A 8/2007
(Continued)

OTHER PUBLICATIONS

Communication Pursuant to Article 94(3) EPC dated May 4, 2020 issued for European Patent Application No. 16893536.9, 7 pages with English translation.
(Continued)

*Primary Examiner* — Guillermo M Rivera-Martinez
(74) *Attorney, Agent, or Firm* — Squire Patton Boggs (US) LLP

(57) ABSTRACT

An evaluation device includes a state determination unit which is configured to determine a state of cells which are an observation target under non-standard conditions on the basis of information acquired from an image of cells under standard conditions.

10 Claims, 16 Drawing Sheets

(51) Int. Cl.
  *C12M 1/00* (2006.01)
  *C12Q 1/68* (2018.01)
  *C12M 1/36* (2006.01)
  *G01N 15/14* (2006.01)
  *G02B 21/36* (2006.01)
  *G16B 45/00* (2019.01)
  *G01N 21/64* (2006.01)
  *C12M 1/34* (2006.01)

(52) U.S. Cl.
  CPC ....... *G01N 15/1475* (2013.01); *G02B 21/367* (2013.01); *G06K 9/00127* (2013.01); *G16B 45/00* (2019.02); *C12M 1/3461* (2013.01); *G01N 21/6458* (2013.01); *G06T 2207/30024* (2013.01)

(56) References Cited

U.S. PATENT DOCUMENTS

| | | | | |
|---|---|---|---|---|
| 2003/0228565 | A1* | 12/2003 | Oestreicher | C12M 41/46 435/4 |
| 2006/0154236 | A1* | 7/2006 | Altschuler | G01N 33/5026 435/4 |
| 2011/0188728 | A1* | 8/2011 | Sammak | G06K 9/00 382/133 |
| 2011/0206262 | A1* | 8/2011 | Sammak | G06T 7/42 382/133 |
| 2011/0206643 | A1 | 8/2011 | Fulga et al. | |
| 2013/0051650 | A1* | 2/2013 | Santamaria-Pang | G16B 40/00 382/133 |
| 2014/0273188 | A1* | 9/2014 | Mohan | G02B 21/00 435/287.2 |
| 2015/0159139 | A1* | 6/2015 | Rezania | C12N 5/067 424/93.7 |
| 2015/0285789 | A1* | 10/2015 | Montano | G01N 33/5073 514/291 |
| 2017/0037483 | A1* | 2/2017 | Hayashi | G01N 21/6486 |
| 2018/0174295 | A1* | 6/2018 | Nakagawa | G06T 7/0016 |
| 2018/0314876 | A1* | 11/2018 | Rubin | C12M 41/46 |
| 2019/0046583 | A1* | 2/2019 | Pan | C12N 5/0696 |
| 2021/0148908 | A1* | 5/2021 | Pangarkar | G01N 33/582 |

FOREIGN PATENT DOCUMENTS

| | | |
|---|---|---|
| WO | WO 2011/118655 A1 | 9/2011 |
| WO | WO 2016/164857 A1 | 10/2016 |

OTHER PUBLICATIONS

Notice of Reasons for Rejection dated Mar. 3, 2020 for Japanese Patent Application No. 2018-503971, 4 pages with English translation.

International Search Report dated Jun. 7, 2016 for PCT Application No. PCT/JP2016/057806, with English translation, 2 pages.

Written Opinion of the International Searching Authority dated Jun. 7, 2016 for PCT Application No. PCT/JP2016/057806, with English translation, 7 pages.

Extended European Search Report dated Oct. 2019 for European Patent Application No. 16893536.9, 9 pages.

Stroh, A., et al.: "Tracking Stem Cell Differentiation in the Setting of Automated Optogenetic Stimulation", Stem Cells Regenerative Medicine, Jan. 1, 2011, vol. 29, No. 1, pp. 78-88, XP055026297.

Communication Pursuant to Article 94(3) EPC dated Nov. 11, 2020 issued for European Patent Application No. 16893536.9, 9 pages.

Communication Pursuant to Article 94(3) EPC dated May 20, 2021 issued for European Patent Application No. 16893536.9, 8 pages.

* cited by examiner

FIG. 4

CELL TYPE STORAGE UNIT 210

| CELL TYPE ID | CELL TYPE |
|---|---|
| CT1 | UNDIFFERENTIATED CELL |
| CT11 | NEURAL STEM CELL |
| CT12 | NEURAL CREST CELL |
| CT21 | NEURAL CELL |
| CT22 | GLIAL PROGENITOR CELL |
| CT23 | PERIPHERAL NEURAL CELL |
| CT31 | OLIGODENDROCYTE |
| CT32 | ASTROCYTE |
| ... | ... |

FIG. 5

PROCESS STORAGE UNIT 220

| PROCESS ID | CELL TYPE OF DIFFERENTIATION ORIGIN | | CELL TYPE OF DIFFERENTIATION DESTINATION | |
|---|---|---|---|---|
| | CELL TYPE ID | CELL TYPE | CELL TYPE ID | CELL TYPE |
| DI11 | CT1 | UNDIFFERENTIATED CELL | CT11 | NEURAL STEM CELL |
| DI12 | CT1 | UNDIFFERENTIATED CELL | CT12 | NEURAL CREST CELL |
| DI21 | CT11 | NEURAL STEM CELL | CT21 | NEURAL CELL |
| DI22 | CT11 | NEURAL STEM CELL | CT22 | GLIAL PROGENITOR CELL |
| DI23 | CT12 | NEURAL CREST CELL | CT23 | PERIPHERAL NEURAL CELL |
| DI31 | CT22 | GLIAL PROGENITOR CELL | CT31 | OLIGODENDROCYTE |
| DI32 | CT22 | GLIAL PROGENITOR CELL | CT32 | ASTROCYTE |
| ... | ... | ... | ... | ... |

FIG. 6

MARKER STORAGE UNIT 230

| MARKER ID | MARKER | MARKER CHARACTERISTICS | RELATING PROCESS |
|---|---|---|---|
| MK1 | OCT3/4 | DECREASE ACCORDING TO PROGRESS OF DIFFERENTIATION OF UNDIFFERENTIATED CELLS | DI11; UNDIFFERENTIATED CELLS → NEURAL STEM CELLS |
| MK2 | NANOG | DECREASE ACCORDING TO PROGRESS OF DIFFERENTIATION OF UNDIFFERENTIATED CELLS | DI11; UNDIFFERENTIATED CELLS → NEURAL STEM CELLS |
| MK3 | NESTIN | INCREASE ACCORDING TO PROGRESS OF DIFFERENTIATION INTO NEURAL STEM CELLS | DI11; UNDIFFERENTIATED CELLS → NEURAL STEM CELLS |
| MK4 | SOX2 | INCREASE ACCORDING TO PROGRESS OF DIFFERENTIATION INTO NEURAL STEM CELLS | DI11; UNDIFFERENTIATED CELLS → NEURAL STEM CELLS |
| ... | ... | ... | ... |

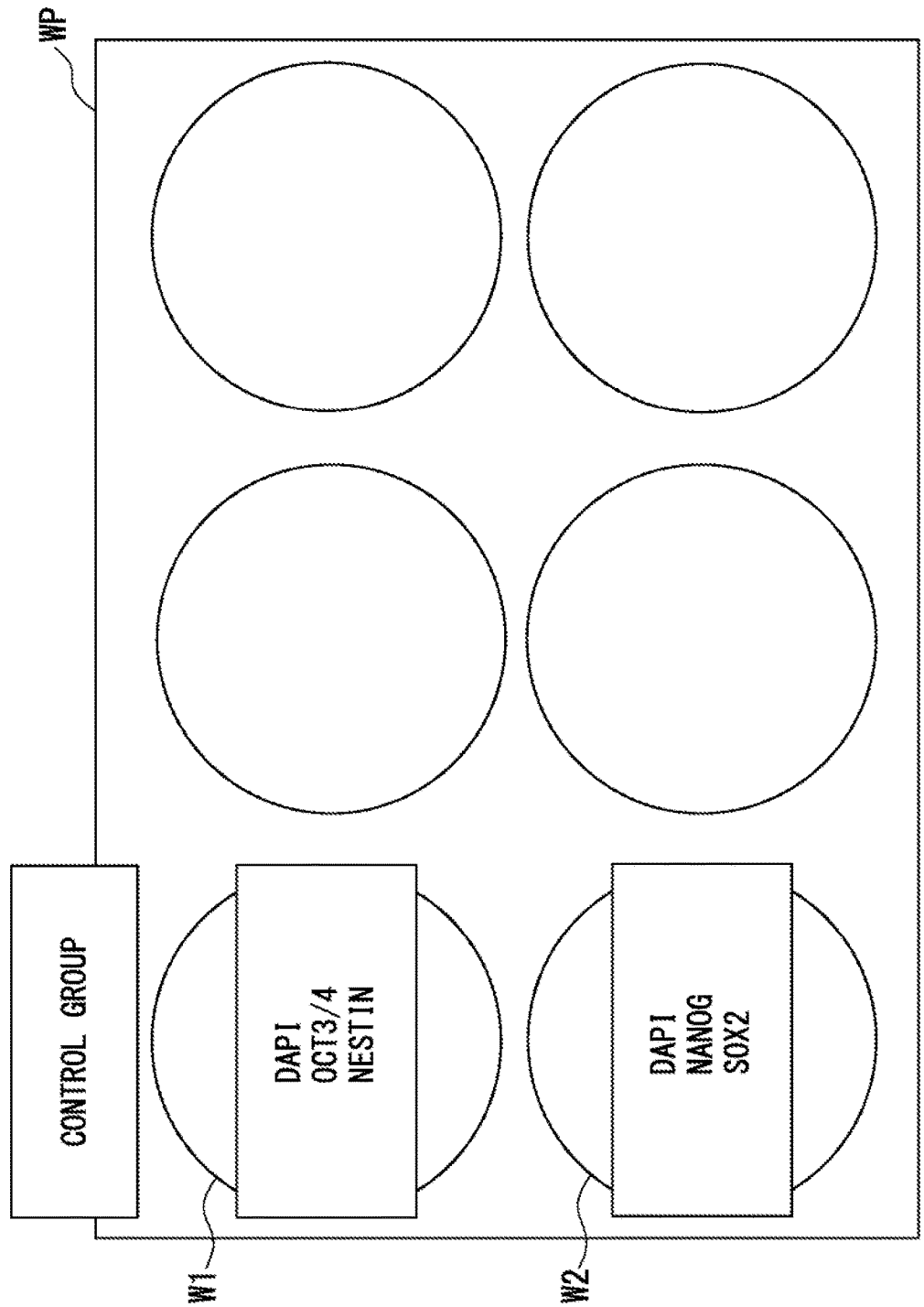

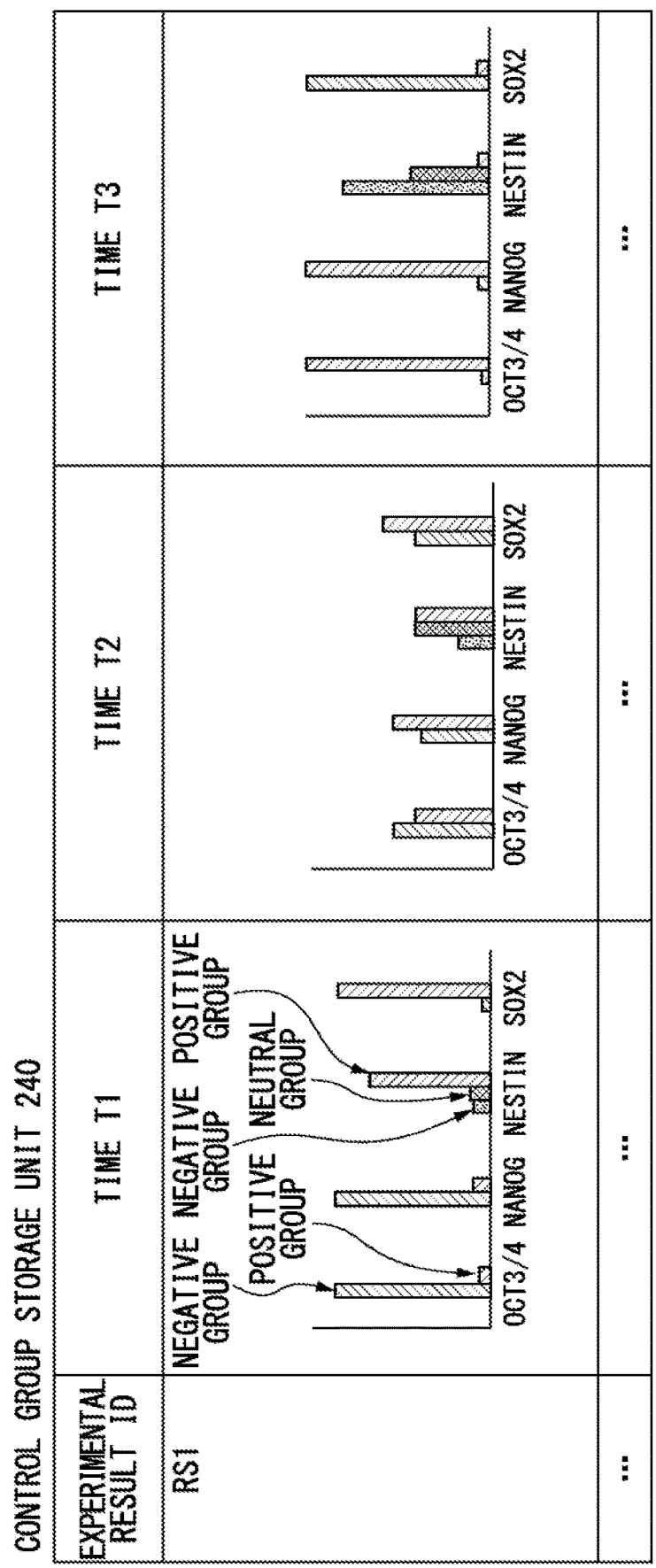

EVALUATION DEVICE, OBSERVATION DEVICE, AND PROGRAM FOR IDENTIFYING CELL DIFFERENTIATION

TECHNICAL FIELD

The present invention relates to an evaluation device, an observation device, and a program.

BACKGROUND ART

In general, technologies for evaluating a state of cultured cells are basic technologies in a wide range of fields including advanced medical fields such as regenerative medicine and screening of drugs and medicines. For example, there is a process of proliferating and differentiating cells in vitro in the field of regenerative medicine. In addition, the aforementioned process requires accurate evaluation of states of cultured cells, such as success or failure of cell differentiation, cell canceration, and presence of absence of infection. As an example, a method for determining a state of cultured cells by processing a captured image of the cells is disclosed (refer to Patent Document 1).

CITATION LIST

Patent Literature

Patent Document 1

Specification of US Patent Application Publication No. 2011/0206643

SUMMARY OF INVENTION

Technical Problem

When a state of cultured cells is evaluated, a control experiment in which experimental results of a control group are compared with those a comparison group may be performed. However, it is impossible, by the aforementioned conventional technology, to accurately evaluate a state of cultured cells such as success or failure of cell differentiation, cell canceration, and presence of absence of infection.

An object of the present invention devised in view of the aforementioned circumstances is to provide an evaluation device, an observation device and a program capable of accurately evaluating a state of cultured cells such as success or failure of cell differentiation, cell canceration, and presence of absence of infection

Solution to Problem

In order to achieve the aforementioned object, one aspect of the present invention is an evaluation device including a state determination unit configured to determine a state of cells which are observation targets under non-standard conditions on the basis of information acquired from an image of cells under standard conditions.

In addition, in order to achieve the aforementioned object, an observation device including the above evaluation device is provided.

Further, in order to achieve the aforementioned object, one aspect of the present invention is a program for causing a computer to execute: an image acquisition step of acquiring a captured image of cells; an observation result acquisition step, under standard conditions, of acquiring an observation result of cells under standard conditions; and a state determination step of determining, on the basis of the image acquired in the image acquisition step and the observation result acquired in the observation result acquisition step under the standard conditions, a state of the cells indicated by the image.

Advantageous Effects of Invention

According to the present invention, it is possible to accurately evaluate a state of cultured cells such as success or failure of cell differentiation, cell canceration, and presence of absence of infection.

BRIEF DESCRIPTION OF DRAWINGS

FIG. 4 is a diagram showing an example of cell types stored in a cell type storage unit of the present embodiment.

FIG. 5 is a diagram showing an example of cell types stored in a Process storage unit of the present embodiment.

FIG. 6 is a diagram showing an example of markers stored in a marker storage unit of the present embodiment.

FIG. 7 is a diagram showing an example of experiment conditions for a control group of the present embodiment.

FIG. 8 is a diagram showing an example of a control group experimental result stored in a control group storage unit of the present embodiment.

DESCRIPTION OF EMBODIMENTS

Figure 1:
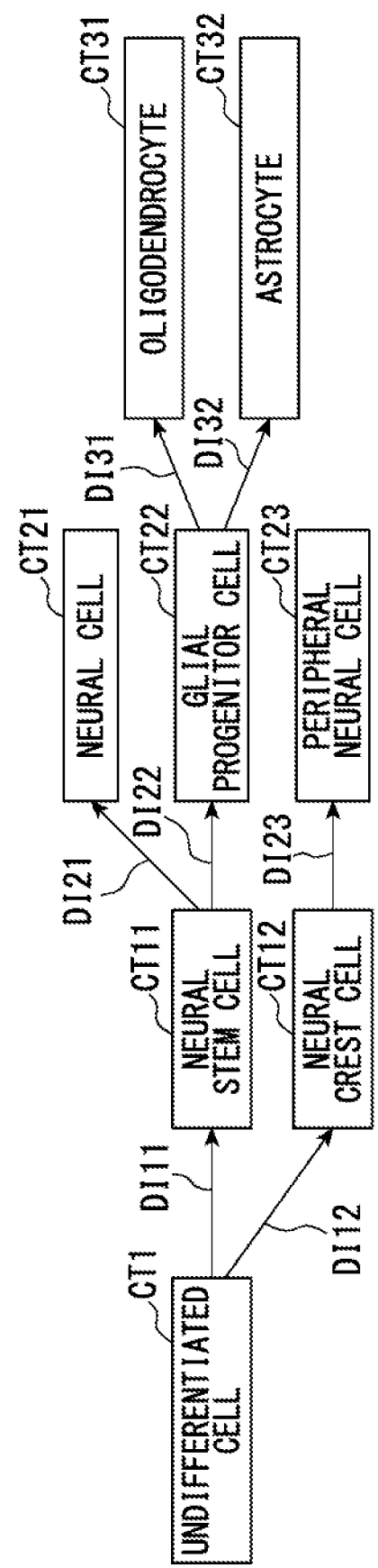
FIG. 1 is a diagram showing an example of differentiation induction into neural cells.

Example of Process of Differentiation Induction: Differentiation Induction of Neural Cells FIG. 1 is a diagram showing an example of differentiation induction into neural cells.

Undifferentiated cells CT1 are differentiated into neural stem cells CT11 via a Process DI11. In addition, the undifferentiated cells CT1 are differentiated into neural crest cells CT12 via a Process DI12. The neural stem cells CT11 are differentiated into neural cells CT21 via a Process DI21. In addition, the neural stem cells CT11 are differentiated into glial progenitor cells CT22 via a Process DI22. The neural crest cells CT12 are differentiated into peripheral neural cells CT23 via a Process DI23. The glial progenitor cells CT22 are differentiated into oligodendrocytes CT31 via a Process DI31. In addition, the glial progenitor cells CT22 are differentiated into astrocytes CT32 via a Process DI32.

Seriously harmful indirect influence of drugs and medicines and environmental substances on the nervous system (particularly, development of the brain) of a fetus or an infant through its mother is called developmental neurotoxicity. Conventionally, evaluation of developmental neurotoxicity requires long-term evaluation using a large number of experimental animals such as rats and thus costs increase. In addition, it is difficult to perform quantitative evaluation of toxicity because comprehensive evaluation of the nervous system is required. Accordingly, a simple and low-cost evaluation mechanism using cells has been needed. Further, when animals are used, there is a high possibility that human toxicity cannot be predicted. Accordingly, it is desirable to perform evaluation using human-originated cells. Moreover, although accurate evaluation mechanisms using human-originated neural cells in the process of generation have not emerged, human multipotential stem cells can be used and thus human-originated neural cells can be used to facilitate evaluation of neural cells.

Developmental neurotoxicity is regarded as being generated because differentiation induction is not normally performed due to toxic compounds, for example. Further, in the case of an infant, occurrence of developmental neurotoxicity may be caused by exposure of the mother to heavy metals, chemical substances and the like, for example, in addition to toxic compounds. Furthermore, there is concern about the influence of medicine taken by a mother on developmental neurotoxicity of a fetus.

In the present embodiment, cultivation of "undifferentiated cells→neural stem cells→neural cells" and cultivation of "undifferentiated cells→neural stem cells→glial progenitor cells" are performed as an example of differentiation induction of a neural cells.

In the present embodiment, immunostaining is performed using a plurality of markers on cells during cultivation in a differentiation induction process. In addition, cells on which immunostaining has been performed using markers are imaged. Evaluation (positivity/negativity determination for each cell) of various markers is performed by analyzing a fluorescent image obtained through imaging. It is possible to perform toxicity evaluation by comparing expression states of various markers when differentiation induction is performed normally with expression states of various markers when developmental neurotoxicity occurs due to a toxic compound.

Such toxicity evaluation will be described in detail. When immunostaining using markers is performed on cells during cultivation, expression states of markers change with the progress of differentiation induction. For example, expression of a certain marker is facilitated with the progress of differentiation induction of cells. In addition, expression of certain other markers is suppressed with the progress of differentiation induction of cells. When a marker of which expression is facilitated with the progress of differentiation induction of cells and a marker of which expression is suppressed with the progress of differentiation induction of cells are used for cells during cultivation, it is possible to evaluate a degree to which differentiation induction has proceeded by evaluating a degree of expression of a marker. Further, when more than one markers suitable for evaluation of the progress of differentiation induction as described above are combined, it is easy to evaluate a degree of the progress of differentiation induction of cells compared to cases in which a single marker is used.

Here, when a substance has been added to cells during cultivation in a differentiation induction process, a progress state of differentiation induction of cells may change compared to cases in which no substance is added. For example, when a substance has been added to cells during cultivation, the progress of differentiation induction of cells may be facilitated or suppressed compared to cases in which no substance is added.

With respect to cells in a differentiation induction process, it is possible to evaluate the influence of a substance on the progress of differentiation induction of cells by comparing an expression state of a marker when the substance has not been added to the cells with an expression state of a marker when the substance has been added. That is, it is possible to perform evaluation of toxicity of a substance through a control experiment performed on marker expression states.

Meanwhile, a differentiation induction process requires a period of several days to several weeks. Accordingly, toxicity evaluation requires observation with time (imaging). Any of the following methods may be used as an imaging method.

1) End-point observation in which a plurality of samples are prepared and cells cultivated for day 1, day 5 and day 10 are stained and observed.

2) Time-lapse observation in which the same samples are observed over time using a fluorescent protein.

In addition, toxicity assay is performed by comparing results of samples (control samples) to which no chemical substances have been added with results of samples to which chemical substances have been added in various concentrations. Here, toxicity evaluation is performed according to "marker identification" for checking "which marker has changed," "toxic effect concentration identification" for checking "a degree of concentration which causes a marker to change" and "effecting time identification" for checking "a time slot in which changes occur," for example.

First Embodiment

Hereinafter, an observation device 1 in a first embodiment will be described. First, a configuration of the observation device 1 will be described with reference to FIG. 2.

[Configuration of Observation Device]

Figure 2:
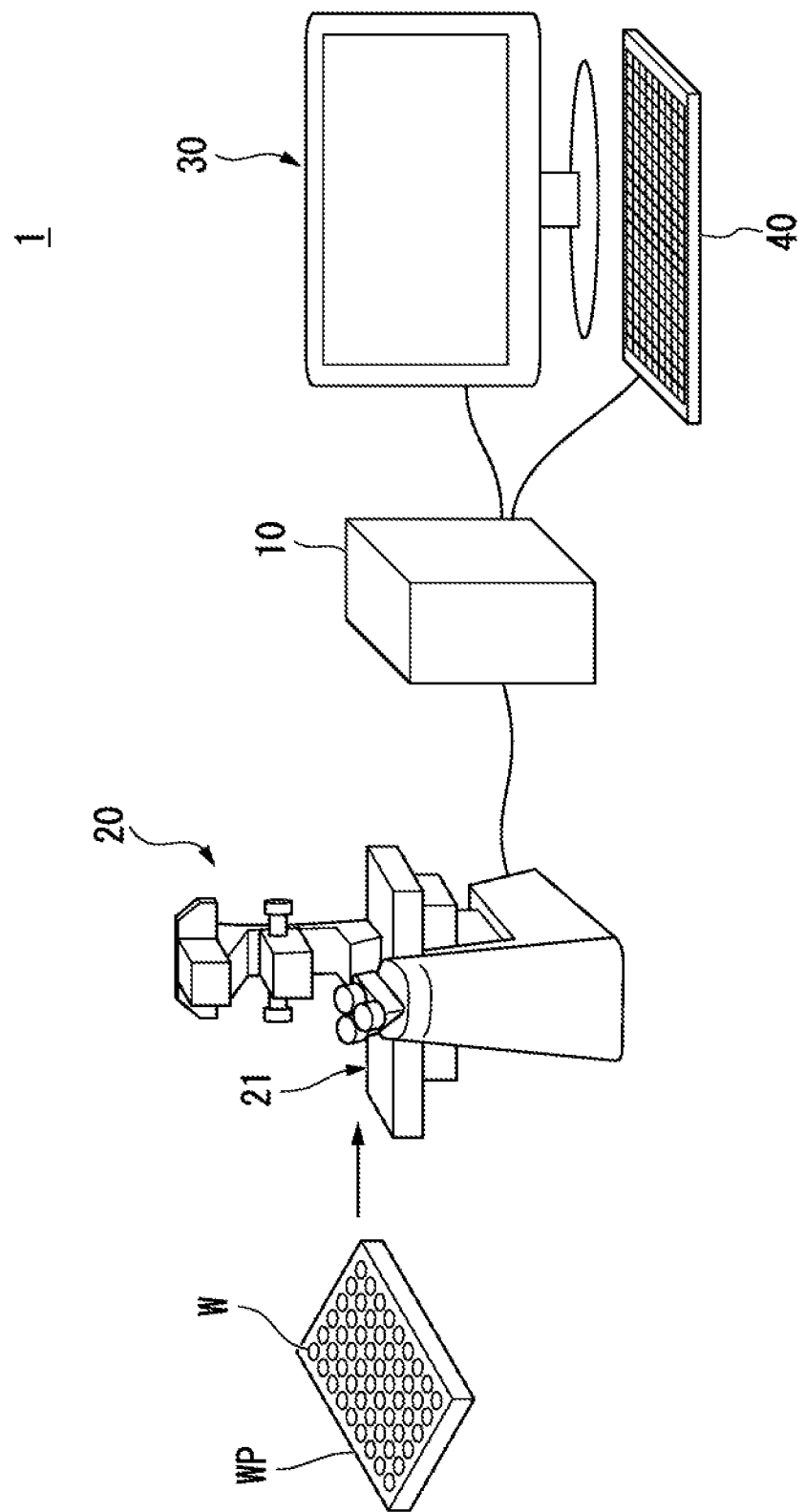
FIG. 2 is a schematic diagram showing an example of a configuration of an observation device according to an embodiment of the present invention.

FIG. 2 is a schematic diagram showing an example of a configuration of an observation device 1 according to an embodiment of the present invention.

The observation device 1 performs image processing on an image acquired by imaging cells and the like. In the following description, an image acquired by imaging cells and the like is simply referred to as a cell image. The observation device 1 includes an evaluation device 10, a microscope device 20, a display unit 30 and an operation detection unit 40.

The microscope device 20 is a biological microscope and includes an electric stage 21 and an imaging unit 22. The electric stage 21 is able to arbitrarily move the position of an imaging target in a predetermined direction (e.g., a certain direction within a two-dimensional plane in the horizontal direction). The imaging unit 22 includes an imaging element such as a charge-coupled device (CCD) or a complementary MOS (CMOS) and images an imaging target on the electric stage 21. Meanwhile, the microscope device 20 may not include the electric stage 21 and may include a stage which is not moved in a predetermined direction.

More specifically, the microscope device 20 has functions of a differential interference contrast microscope (DIC), a phase-contrast microscope, a fluorescent microscope, a confocal microscope, a super-resolution microscope and the like, for example. The microscope device 20 images a cultivation container placed on the electric stage 21. For example, the cultivation container is a well plate WP. The microscope device 20 radiates light to cells cultivated in a plurality of wells W included in the well plate WP to image transmitted light which has passed through cells as images of cells. Accordingly, images of cells, such as a transmitted DIC image, a phase-contrast image, a dark field image, a bright field image and the like may be obtained. Further, fluorescence emitted from biomaterials is imaged as an image of cells by radiating exciting light which excites fluorescent materials to cells. In addition, the microscope device 20 may image fluorescence emitted from a color-development substance contained in a biomaterial and fluorescence emitted according to bonding of a substance having chromophores to a biomaterial as images of the aforementioned cells. Accordingly, the observation device 1 is able to acquire fluorescent images, confocal images and super-resolution images. Meanwhile, a method of acquiring images of cells is not limited to an optical microscope.

The well plate WP has the plurality of wells W. The well plate WP has 12×8 (96) wells W in this example. Cells are cultivated in the wells W under specific experimental conditions. The specific experimental conditions include temperature, humidity, a cultivation period, an elapsed time from provision of a stimulus, the type and intensity of a provided stimulus, presence or absence of a stimulus, induction of biological properties, and the like. Stimuli include physical stimuli such as electricity, sound waves, magnetism and light, chemical stimuli according to injection of substances or medicines, and the like, for example. Further, biological properties are properties representing a cell differentiation phase and form, the number of cells, and the like.

The display unit 30 includes a liquid crystal display or the like and displays operation results obtained by the evaluation device 10.

The operation detection unit 40 includes a keyboard, a mouse which is not shown, and the like and detects an operation for the evaluation device 10.

Functional Configuration of Evaluation Device 10

Figure 3:
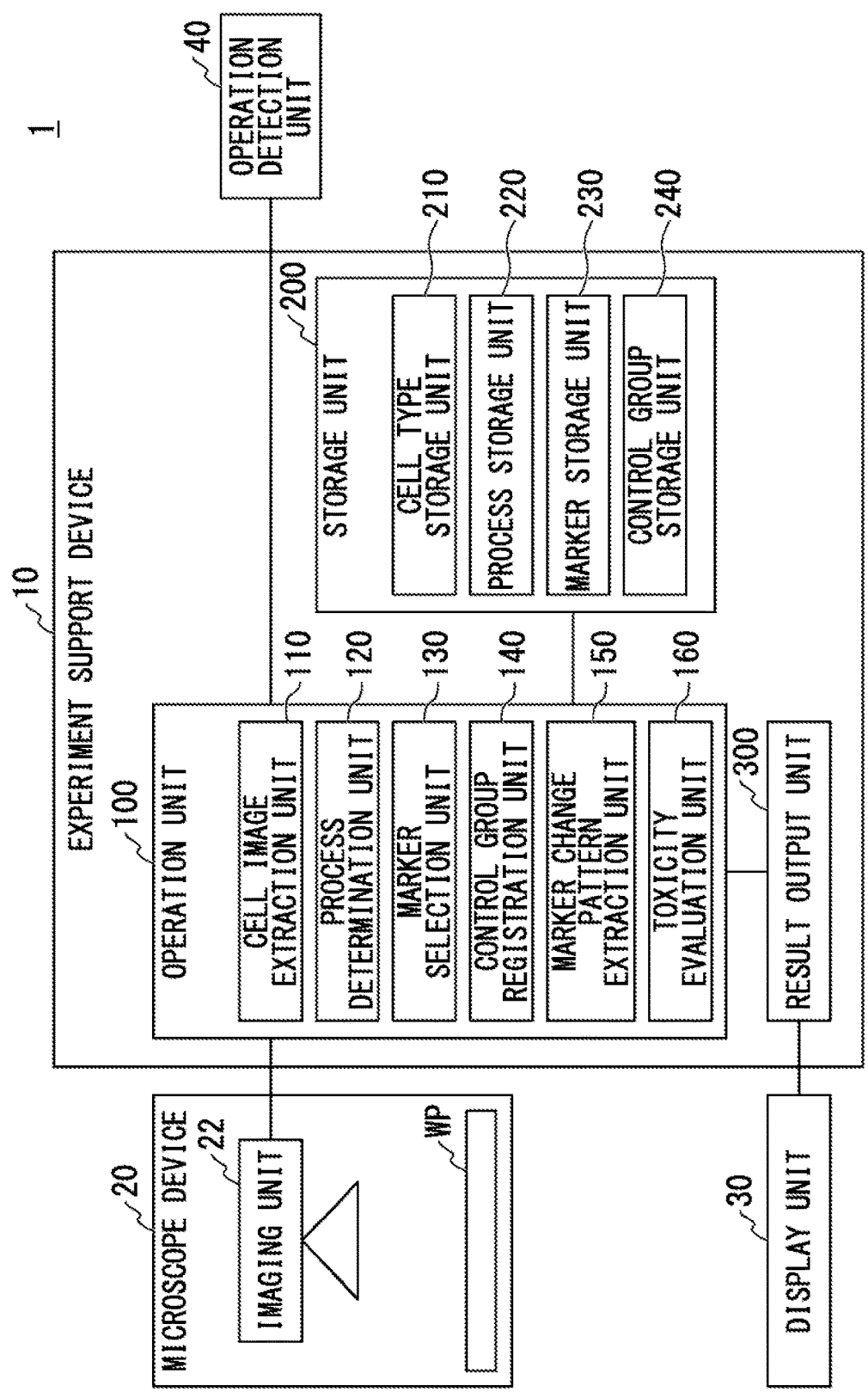
FIG. 3 is a block diagram showing a functional configuration of an evaluation device of the present embodiment.

FIG. 3 is a block diagram showing a functional configuration of the evaluation device 10 of the present embodiment. The evaluation device 10 includes an operation unit 100 and a storage unit 200.

The storage unit 200 includes a cell type storage unit 210, a Process storage unit 220, a marker storage unit 230 and a control group storage unit 240.

The cell type storage unit 210 stores information indicating types of cells, that is, cell types. Specifically, the cell type storage unit 210 stores cell type IDs for identifying cell types and names of the cell types correlated to the cell type IDs.

FIG. 4 is a diagram showing an example of cell types stored in the cell type storage unit 210 of the present embodiment. In this example, a cell type ID_CT1 and a cell type name "undifferentiated cell" are associated with each other and stored in the cell type storage unit 210. In addition, a cell type ID_CT11 and a cell type name "neural stem cell," and a cell type ID_CT12 and a cell type name "neural crest cell" are associated with each other and stored in the cell type storage unit 210. Further, a cell type ID_CT21 and a cell type name "neural cell," a cell type ID_CT22 and a cell type name "glial progenitor cell" and a cell type ID_CT23 and a cell type name "peripheral neural cell" are associated with each other and stored in the cell type storage unit 210. Moreover, a cell type ID_CT31 and a cell type name "oligodendrocyte" and a cell type ID_CT32 and a cell type name "astrocyte" are associated with each other and stored in the cell type storage unit 210.

In the following description, the cell type "undifferentiated cell" is also described as an undifferentiated cell CT1. In addition, the cell type "neural stem cell," the cell type "neural crest cell", the cell type "neural cell," the cell type "glial progenitor cell" and the cell type "peripheral neural cell" are also described as a neural stem cell CT11, a neural crest cell CT12, a neural cell CT21, a glial progenitor cell T22 and a peripheral neural cell CT23, respectively. Further, the cell type "oligodendrocyte" and the cell type "astrocyte" are also described as an oligodendrocyte CT31 and an astrocyte CT32, respectively.

The Process storage unit 220 stores information representing Process of cell differentiation. Specifically, Process IDs for identifying Process, cell type IDs and names of cell types of differentiation origins, and cell type IDs and names of cell types of differentiation destinations are associated with one another and stored in the Process storage unit 220.

FIG. 5 is a diagram showing an example of cell types stored in the Process storage unit 220 of the present embodiment. In this example, a Process ID_DI11 and a cell type ID_CT1 and a name "undifferentiated cell" of a cell type of a differentiation origin, and a cell type ID_CT11 and a name "neural stem cell" of a cell type of a differentiation destination are associated and stored in the Process storage unit 220. In addition, a Process ID_DI12 and the cell type ID_CT1 and the name "undifferentiated cell" of the cell type of the differentiation origin, and a cell type ID_CT12 and a name "neural crest cell" of a cell type of a differentiation destination are associated and stored in the Process storage unit 220. Regarding Process DI21, DI22, DI23, DI31 and DI32 cell types of differentiation origins and cell types of differentiation destinations are also associated and stored in the Process storage unit 220 as described above and shown in FIG. 5.

The marker storage unit 230 stores names and characteristics of markers and information on related cells. Specifically, marker IDs for identifying markers, marker names, characteristics of markers, and cell types relating to markers are associated and stored in the marker storage unit 230. Here, markers are reagents, antibodies and the like for evaluating states of cells, particularly, differentiation states of cells.

FIG. 6 is a diagram showing an example of markers stored in the marker storage unit 230 of the present embodiment. In this example, a marker ID_MK1, a marker name "OCT3/4," a marker characteristic "decreasing according to progress of differentiation of undifferentiated cells" and a related cell type "CT1; undifferentiated cell" are associated and stored in the marker storage unit 230. In addition, a marker ID_MK2, a marker name "NANOG," the marker characteristic "decreasing according to progress of differentiation of undifferentiated cells" and the related cell type "CT1; undifferentiated cell" are associated and stored in the marker storage unit 230. Further, a marker ID_MK3, a marker name "NESTIN," a marker characteristic "increasing according to progress of differentiation into neural stem cells" and a related cell type "CT11; neural stem cell" are associated and stored in the marker storage unit 230. Further, the marker ID_MK4, a marker name "SOX2," the marker characteristic "increasing according to progress of differentiation into neural stem cells" and the related cell type "CT11; neural stem cell" are associated and stored in the marker storage unit 230.

That is, markers and information representing characteristics of the markers are associated and stored in the marker storage unit 230.

In addition, the storage unit 200 has an image processing program used for image processing of a cell image PCL and a control program of the microscope device 20 stored therein in advance.

Referring back to FIG. 3, the operation unit 100 includes a central processing unit (CPU) and drives each unit of the microscope device 20 according to the control program stored in the storage unit 200. Details of control of the microscope device 20 according to the operation unit 100 are known and thus description thereof is omitted.

Further, the operation unit 100 includes a cell image extraction unit 110, a Process determination unit 120, a marker selection unit 130, a control group registration unit 140, a marker change pattern extraction unit 150 and a toxicity evaluation unit 160 as functional units thereof.

The cell image extraction unit 110 extracts a cell image from images captured by the imaging unit 22. Specifically, the imaging unit 22 captures images of cells cultivated in the wells W of the well plate WP. The images captured by the imaging unit 22 include an image of cells, that is, a cell image. The cell image extraction unit 110 extracts a cell image from the images captured by the imaging unit 22 by performing image processing on the images captured by the imaging unit 22 through a known method such as pattern matching. The cell image extraction unit 110 provides the extracted cell image to each functional unit of the operation unit 100.

The Process determination unit 120 determines a Process which is an experiment target among Process of cell differentiation. Here, the operation detection unit 40 receives an operation of a user who uses the evaluation device 10. The operation detection unit 40 outputs information representing the operation received from the user to the operation unit 100. In this example, the user designates a Process of cell differentiation which is an experiment target according to a cell type of a start point of the Process of cell differentiation and a cell type of an end point thereof. As an example, when the operation detection unit 40 is a keyboard, the user designates the cell type of the start point and the cell type of the end point by operating the keyboard. The operation detection unit 40 detects an operation of the user to designate the cell type of the start point and an operation of the user to designate the cell type of the end point. The operation detection unit 40 outputs information representing the detected operations to the operation unit 100.

The Process determination unit 120 acquires the information representing the operations from the operation detection unit 40 and determines the Process which is the experiment target on the basis of the cell type of the start point and the cell type of the end point included in the information. Specifically, the Process determination unit 120 searches the Process storage unit 220 using the cell type of the start point and the cell type of the end point acquired from the operation detection unit 40 as search keys. The Process determination unit 120 correlates the cell type of the start point used as a search key to a cell type of a differentiation origin and correlates the cell type of the end point used as a search key to a cell type of a differentiation destination. The Process determination unit 120 extracts a Process ID associated with the cell type of the correlated differentiation origin and the cell type of the differentiation destination among Process IDs stored in the Process storage unit 220 as a Process ID indicating the Process which is the experiment target. For example, when the cell type of the start point acquired from the operation detection unit 40 is the undifferentiated cell CT1 and the cell type of the end point is the neural stem cell CT11, the Process determination unit 120 extracts a Process ID_DI11 as a Process ID of the Process which is the experiment target. That is, in this case, the Process determination unit 120 determines the Process ID_DI11 as the Process ID of the Process which is the experiment target.

In addition, the Process determination unit 120 may determine imaging conditions (observation conditions) for cells along with determination of the Process which is the experiment target. For example, the Process determination unit 120 may determine an imaging time according to the determined Process. Specifically, when the Process determination unit 120 determines a Process of differentiation from the undifferentiated cell CT1 to the neural stem cell CT11 as a Process which is an experiment target, the Process determination unit 120 may determine an imaging time according to a speed of differentiation from the undifferentiated cell CT1 to the neural stem cell CT11. Further, this imaging time may be associated with the Process ID and stored in the Process storage unit 220 in advance. In this case, the Process determination unit 120 may acquire the imaging time associated with the Process which is the experiment target from the Process storage unit 220 along with determination of the Process which is the experiment target.

Further, the Process determination unit 120 may extract a plurality of Process IDs as Process IDs of Process which are experiment targets. As an example, when the cell type of the start point acquired from the operation detection unit 40 is the undifferentiated cell CT1 and the cell type of the end point is the neural cell CT21, the Process determination unit 120 extracts the Process ID_DI11 and the Process ID_DI21 as Process IDs of the Process which are experiment targets.

The marker selection unit 130 selects a marker suitable for a Process which is an experiment target. Specifically, the marker selection unit 130 acquires a Process ID of a Process determined by the Process determination unit 120 as a Process which is an experiment target from the Process determination unit 120. The marker selection unit 130 searches the marker storage unit 230 using the acquired Process ID as a search key to extract a marker. Here, the extracted marker is a marker suitable for the Process which is the experiment target.

As an example, a case in which a Process which is an experiment target is the Process ID_DI11 will be described.

In this case, the marker selection unit 130 acquires the Process ID_DI11 from the Process determination unit 120. The marker selection unit 130 searches the marker storage unit 230 using the Process ID_DI11 as a search key. As a result of the searching, the marker selection unit 130 acquires the marker ID_MK1, marker ID_MK2, marker ID_MK3 and marker ID_MK4. That is, the marker selection unit 130 selects "OCT3/4," "NANOG," "NESTIN" and "SOX2" as markers suitable for the Process which is the experiment target.

That is, the marker selection unit 130 selects markers for evaluating cell differentiation states according to a cell differentiation process. Here, the cell differentiation process includes a time or a period in differentiation, Process to which cells are differentiated, and the like. That is, the marker selection unit 130 is able to select markers for evaluating cell differentiation states according to a cell state in a certain time in cell differentiation. Further, the marker selection unit 130 is able to select markers for evaluating cell differentiation states according to a Process to which cells are differentiated.

Furthermore, a Process to which cells are differentiated may be determined by a first cell type (e.g., a cell type of a start point and a cell type of a differentiation origin) and a second cell type (e.g., a cell type of an end point and a cell type of a differentiation destination). That is, the marker selection unit 130 may select markers according to the first cell type and the second cell type.

Further, the marker selection unit 130 may select markers according to a process on the basis of information representing characteristics of markers stored in the marker storage unit 230 and the process.

The control group registration unit 140 registers experimental results with respect to a control group by storing the experimental results with respect to the control group in the control group storage unit 240. Here, experiments on a control group will be described.

Experiments on Control Group

A control group is a controlled group among experimental groups in a comparison experiment (or control experiment). For example, an experimental result with respect to a control group is an experimental result of cell differentiation under a condition in which no substance is added to cells, which is a standard condition. In this example, the influence of a substance in a predetermined concentration on cells when the substance has been added to cells in process of differentiation is determined through a control experiment of comparing a group (control group) to which the substance has not been added with a group (comparison group) under a non-standard condition in which the substance has been added.

FIG. 7 is a diagram showing an example of an experiment situation of a control group of the present embodiment. An undifferentiated cell CT1-1 to which a fluorescent dye DAPI of nuclear staining, OCT3/4 and NESTIN are provided as markers is sown in a well W1 of a well plate WP. An undifferentiated cell CT1-2 to which the fluorescent dye DAPI of nuclear staining, NANOG and SOX2 are provided as markers is sown in a well W2 of the well plate WP. Meanwhile, DAPI is a kind of marker which dyes the nucleus of a cell. Although DAPI is an exemplary example of a fluorescent dye of nuclear staining in the present embodiment, available fluorescent dyes are not limited thereto and, for example, Hoechst and the like may be used.

The well plate WP including the well W1 and the well W2 is placed on the electric stage 21 of the microscope device 20. The imaging unit 22 captures an image of each well W of the well plate WP placed on the electric stage 21 at certain intervals. In this example, the imaging unit 22 captures an image of each well W of the well plate WP at a time T1, a time T2 and a time T3 over time. Cells sown in wells W include cells (negative group) which do not react to markers and cells (positive group) which reacts to markers. The proportions of the negative group and the positive group in cells in the wells W change with the progress of cell differentiation.

FIG. 8 is a diagram showing an example of experimental results with respect to a control group stored in the control group storage unit 240 of the present embodiment.

A case in which undifferentiated cells CT1 are differentiated to neural stem cells CT11 will be described as an example. Cells in wells W are differentiated from undifferentiated cells CT1 to neural stem cells CT11 for a period from a time T1 to a time T3. OCT3/4 and NANOG among markers react to the neural stem cells CT11 rather than the undifferentiated cells CT1. NESTIN and SOX2 among markers react to the undifferentiated cells CT1 rather than the neural stem cells CT11.

At the time T1, most of the cells in the wells W are undifferentiated cells CT1. In this case, a negative group for OCT3/4 and NANOG is larger in quantity than a positive group among cells in the well W1 at the time T1. Further, a positive group for NESTIN and SOX2 is larger in quantity than a negative group among cells in the well W2 at the time T1.

At the time T2, the proportions of undifferentiated cells CT1 and neural stem cells CT11 in cells in the wells W are equal. In this case, the proportions of a negative group and a positive group for OCT3/4 and NANOG among cells in the well W1 are equal at the time T2. Further, the proportions of a negative group and a positive group for NESTIN and SOX2 among cells in the well W2 are equal at the time T2.

At the time T3, most of the cells in the wells W are neural stem cells CT11. In this case, a positive group for OCT3/4 and NANOG is larger in quantity than a negative group among cells in the well W1 at the time T3. Further, a negative group for NESTIN and SOX2 is larger in quantity than a positive group among cells in the well W2 at the time T3.

Referring back to FIG. 3, the imaging unit 22 captures an image of each well W at the time T1, time T2 and time T3. The cell image extraction unit 110 extracts a cell image from images captured by the imaging unit 22. Here, cells in wells W have been fluorescent-dyed by DAPI which is a marker. DAPI is strongly bonded to deoxyribonucleic acid (DNA). Accordingly, when exciting light such as ultraviolet light is radiated to cells in the wells W, the nucleuses of the cells emit fluorescence. In this case, the cell image extraction unit 110 is able to extract a cell image by extracting a fluorescent part from the images captured by the imaging unit 22.

That is, the imaging unit 22 outputs a cell image obtained by capturing an image of cells cultivated using markers selected by the marker selection unit 130 as an experimental result.

The control group registration unit 140 stores the cell image extracted by the cell image extraction unit 110 in the control group storage unit 240 as an experimental result with respect to a control group.

The control group registration unit 140 associates an experimental result ID for identifying an experimental result with an experimental result with respect to a control group at a certain time and stores the associated experimental result ID and the result in the control group storage unit 240. In this example, an experimental result ID_RS1 and experimental results with respect to the control group at the time T1, time T2 and time T3 are associated and stored in the control group storage unit 240. That is, the control group storage unit 240 is an experimental result storage unit in which experimental results of cell differentiation under standard conditions using markers selected by the marker selection unit 130 are stored.

The marker change pattern extraction unit 150 extracts a marker change pattern of a control group from experimental results with respect to the control group stored in the control group storage unit 240. A case in which a marker change pattern of a control group is extracted with respect to an experimental result ID_RS1 will be described as an example. In this case, the marker change pattern extraction unit 150 acquires the experimental result ID_RS1. For example, the experimental result ID_RS1 is provided to the marker change pattern extraction unit 150 by a user of the evaluation device 10 operating the operation detection unit 40. The marker change pattern extraction unit 150 searches the control group storage unit 240 using the acquired experimental result ID_RS1 as a search key. The marker change pattern extraction unit 150 extracts an experimental result acquired as a search result as a marker change pattern of the control group.

The toxicity evaluation unit 160 evaluates toxicity of a corresponding substance by comparing an experimental result with respect to a control group with an experimental result with respect to a comparison group. Specifically, the toxicity evaluation unit 160 compares a marker change pattern of the control group extracted by the marker change pattern extraction unit 150 with a marker change pattern of cells when a substance has been added in a predetermined concentration to the cells in process of differentiation. If there is no significant difference between the marker change pattern of the control group and the marker change pattern of the cells when the substance has been added in the predetermined concentration, the toxicity evaluation unit 160 evaluates that the toxicity of this substance is low. In addition, if there is a significant difference between the marker change pattern of the control group and the marker change pattern of the cells when the substance has been added in the predetermined concentration, the toxicity evaluation unit 160 evaluates that the toxicity of this substance is high.

Toxicity evaluation performed by the toxicity evaluation unit 160 will be described in more detail. Here, when differentiation induction proceeds, a marker of which expression is suppressed is also described as a suppressed marker. When differentiation induction proceeds, a marker of which expression is facilitated is also described as a facilitated marker. The toxicity evaluation unit 160 compares the marker change pattern of the control group with the marker change pattern of the cells when the substance has been added in the predetermined concentration.

When a suppressed marker is used, the marker change pattern of cells when the substance has been added in the predetermined concentration represents toxicity according to addition of the substance when marker expression is facilitated along with the progress of differentiation induction.

In addition, when a facilitated marker is used, the marker change pattern of cells when the substance has been added in the predetermined concentration represents toxicity according to addition of the substance when marker expression is suppressed along with the progress of differentiation induction.

Here, the concentration of a substance added to cells affects the progress of differentiation induction of cells. This relates to the capacity of a medicine taken by a person. For example, when the concentration of a substance added to cells is low, NESTIN positive cells decrease in quantity compared to a case in which the concentration of the substance added to cells is high and thus differentiation induction is suppressed. In addition, when the concentration of a substance added to cells is high, NESTIN positive cells increase in quantity compared to a case in which the concentration of the substance added to cells is low and thus differentiation induction is facilitated.

The toxicity evaluation unit 160 determines a state of a second experimental result on the basis of a first experimental result under standard conditions stored in the control group storage unit 240 and the second experimental result of cell differentiation using markers selected by the marker selection unit 130.

In other words, the toxicity evaluation unit 160 may be a state determination unit which determines a state of an experimental result on the basis of a result of control experiment.

In addition, the toxicity evaluation unit 160 may be a state determination unit which determines a state of a cell differentiation process indicated by a differentiation process image which is a captured image of a cell differentiation process on the basis of the differentiation process image and an experimental result of cell differentiation under the standard conditions.

A result output unit 300 outputs an operation result of the operation unit 100 to the outside of the evaluation device 10. In this example, the result output unit 300 displays markers selected by the marker selection unit 130 through the display unit 30. In addition, the result output unit 300 displays a marker change pattern of a control group extracted by the marker change pattern extraction unit 150 through the display unit 30. Further, when the Process determination unit 120 determines an imaging time of an image of a differentiation process, the result output unit 300 displays the imaging time determined by the Process determination unit 120 through the display unit 30.

Operations of Evaluation Device 10

Next, operations of the evaluation device 10 will be described with reference to FIGS. 9 to 17.

Figure 9:
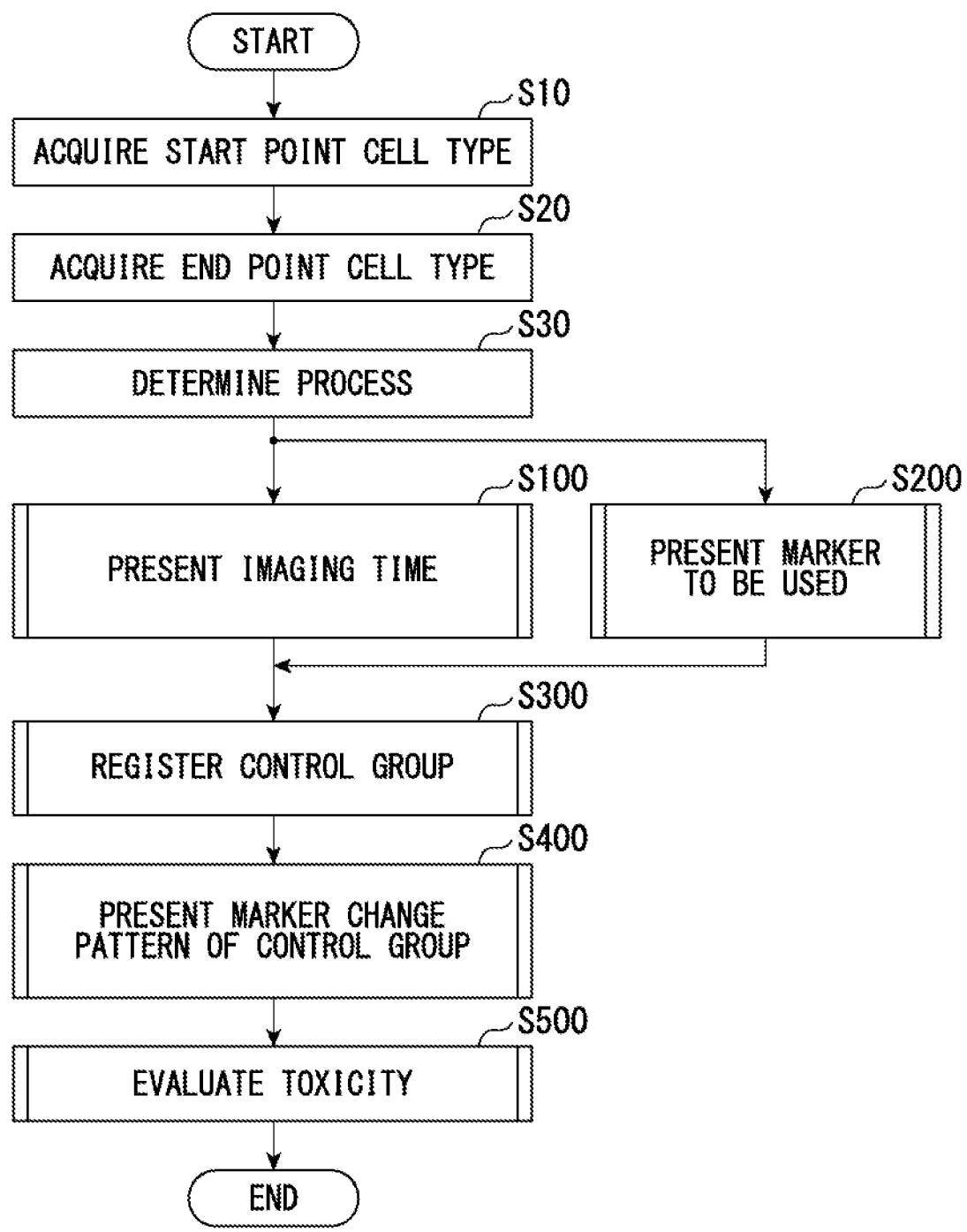
FIG. 9 is a diagram showing an example of the overall operation of the evaluation device of the present embodiment.

FIG. 9 is a diagram showing an example of the overall operation of the evaluation device 10 of the present embodiment. In this example, a case in which the evaluation device 10 supports experiments on a control group and experiments on a comparison group in a control experiment will be described. In the case of this example, the user of the evaluation device 10 determines a Process which is an experiment target by inputting a start point cell type and an end point cell type through a keyboard included in the operation detection unit 40.

Determination of Process which is Experiment Target

The Process determination unit 120 acquires a start point cell type and an end point cell type from the operation detection unit 40 (step S10 and step S20). The Process determination unit 120 determines a Process which is an experiment target on the basis of the start point cell type and the end point cell type acquired in step S10 and step S20 (step S30).

Presentation of Imaging Time

Next, an operation of presenting an imaging time (step S100; steps S110 to S130) performed by the evaluation device 10 will be described.

Figure 10:
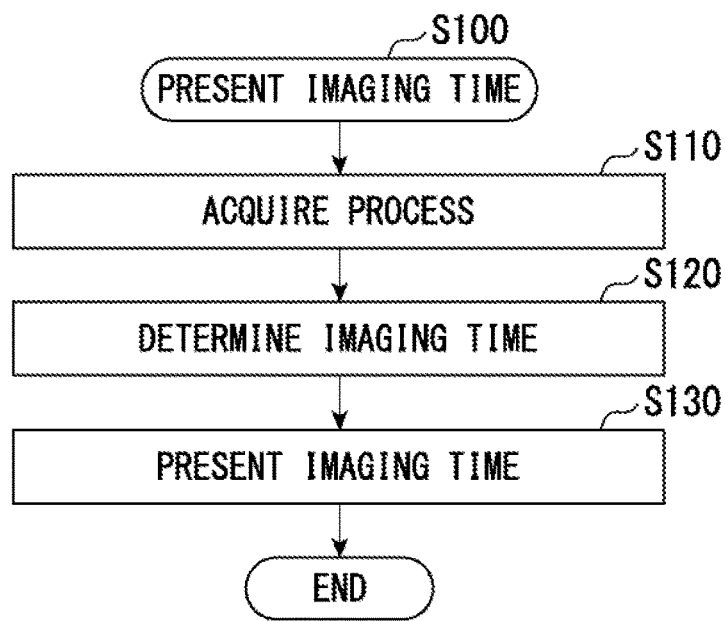
FIG. 10 is a diagram showing an example of an operation of presenting an imaging time performed by the evaluation device of the present embodiment.

FIG. 10 is a diagram showing an example of the operation of presenting an imaging time performed by the evaluation device 10 of the present embodiment. The Process determination unit 120 acquires the Process determined in step S30 (step S110). The Process determination unit 120 determines a time at which the imaging unit 22 will image wells W, that is, an imaging time with respect to the acquired Process which is an experiment target (step S120). For example, when the Process which is an experiment target is the Process ID_DI11, the aforementioned time T1, time T2 and time T3 are determined as imaging times.

The Process determination unit 120 outputs the determined imaging time to the result output unit 300. The result output unit 300 displays information on the imaging time through the display unit 30 (step S130).

Presentation of Marker to be Used

Next, an operation of presenting a marker to be used (step S200; steps S210 to S230) performed by the evaluation device 10 will be described.

Figure 11:
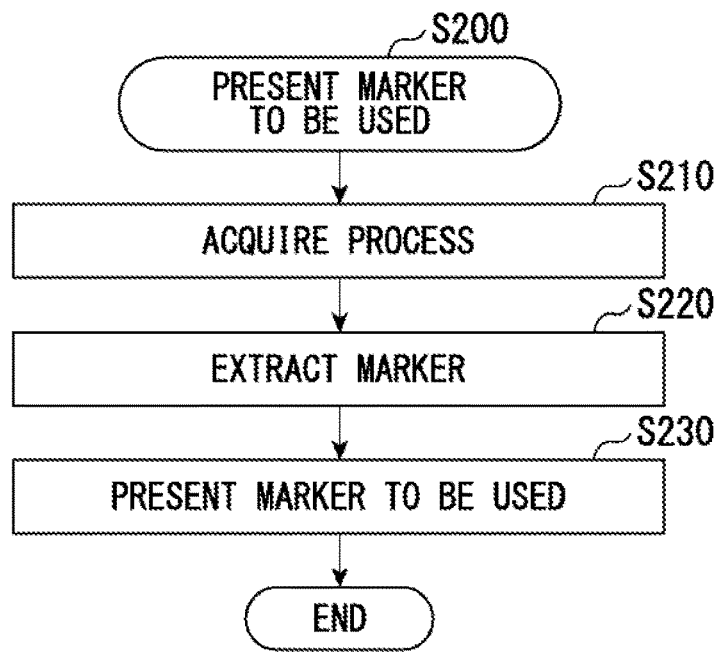
FIG. 11 is a diagram showing an example of an operation of presenting an imaging time performed by the evaluation device of the present embodiment.

FIG. 11 is a diagram showing an example of the operation of presenting a marker to be used performed by the evaluation device 10 of the present embodiment. The marker selection unit 130 acquires the Process determined by the Process determination unit 120 in step S30 (step S210). The marker selection unit 130 extracts a marker suitable for the Process which is an experiment target from the marker storage unit 230 on the basis of the Process acquired in step S210 (step S220). The marker selection unit 130 outputs information on the extracted marker to the result output unit 300. The result output unit 300 displays the marker information through the display unit 30 (step S230).

The imaging time and the marker to be used with respect to the Process which is an experiment target are displayed through the display unit 30 through steps S100 and S200. Since the imaging time and the marker to be used are displayed, the user of the evaluation device 10 is able to aware of an appropriate imaging time and an appropriate marker with respect to the Process which is an experiment target. In addition, the user of the evaluation device 10 is able to perform experiments on the control group and the comparison group under the same conditions by performing control experiments using the displayed imaging time and marker.

Registration of Experimental Result with Respect to Control Group

Figure 12:
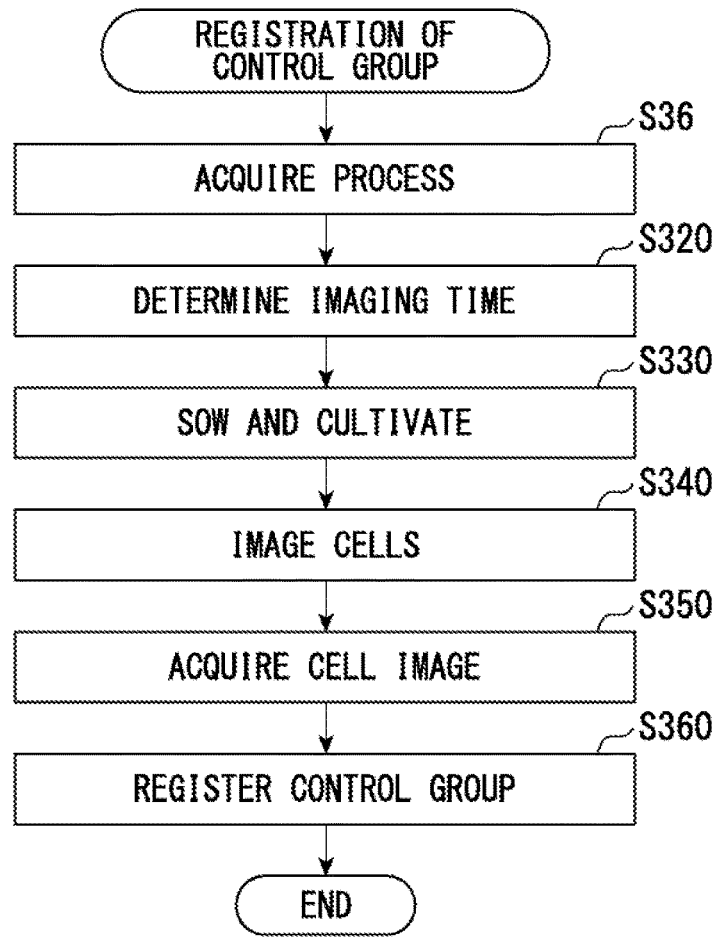
FIG. 12 is a diagram showing an example of an operation of registering experimental results with respect to a control group performed by the evaluation device of the present embodiment.

FIG. 12 is a diagram showing an example of an operation of registering an experimental result with respect to a control group, performed by the evaluation device 10 of the present embodiment.

A case in which the user of the evaluation device 10 performs an experiment on the control group using an imaging time and a marker displayed on the display unit 30 will be described as an example. In this case, the user inputs the Process which is an experiment target through the keyboard included in the operation detection unit 40.

The control group registration unit 140 acquires the Process which is an experiment target from the operation detection unit 40 (step S310). The control group registration unit 140 determines an imaging time on the basis of the acquired Process (step S320). Determination of the imaging time may be performed by the Process determination unit 120, as described above.

The user dyes cells using the marker displayed in step S200. The user sows the cells in wells W and starts cultivation (step S330). The imaging unit 22 of the microscope device 20 images each well W of the well plate WP at the imaging time determined in step S320 (step S340). The cell image extraction unit 110 extracts a cell image from images captured in step S340. The control group registration unit 140 acquires the extracted cell image (step S350). The control group registration unit 140 stores the cell image acquired in step S350 in the control group storage unit 240 as an experimental result with respect to the control group. That is, the control group registration unit 140 registers the control group (step S360).

Further, the control group registration unit 140 may store a result obtained by processing the cell image through a known image processing means in the control group storage unit 240 as an experimental result with respect to the control group.

Presentation of Marker Change Pattern of Control Group

Figure 13:
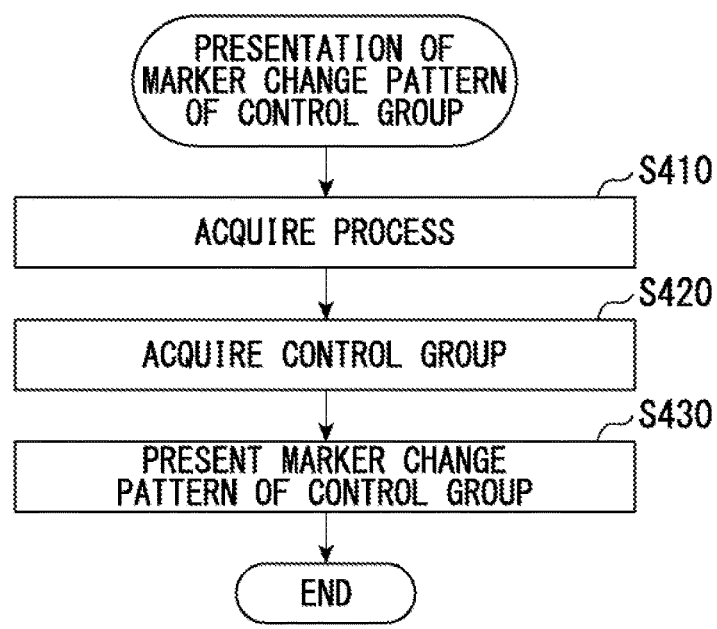
FIG. 13 is a diagram showing an example of an operation of presenting a marker variation pattern of a control group performed by the evaluation device of the present embodiment.

FIG. 13 is a diagram showing an example of an operation of presenting a marker change pattern of a control group, performed by the evaluation device 10 of the present embodiment. In this example, the user of the evaluation device 10 inputs the Process which is an experiment target through the keyboard included in the operation detection unit 40.

The marker change pattern extraction unit 150 acquires the Process input by the user through the keyboard from the operation detection unit 40 (step S410). The marker change pattern extraction unit 150 searches the control group storage unit 240 on the basis of the Process acquired in step S410. Further, when experimental result IDs and Process IDs are associated and stored in the control group storage unit 240, the marker change pattern extraction unit 150 searches the control group storage unit 240 using the Process acquired in step S410 as a search key. The marker change pattern extraction unit 150 acquires an experimental result with respect to the control group, obtained as a search result (step S420). The marker change pattern extraction unit 150 outputs the experimental result with respect to the control group acquired in step S420 to the result output unit 300 as a marker change pattern of the control group. The result output unit 300 displays the marker change pattern of the control group through the display unit 30 (step S430).

Evaluation Toxicity

Figure 14:
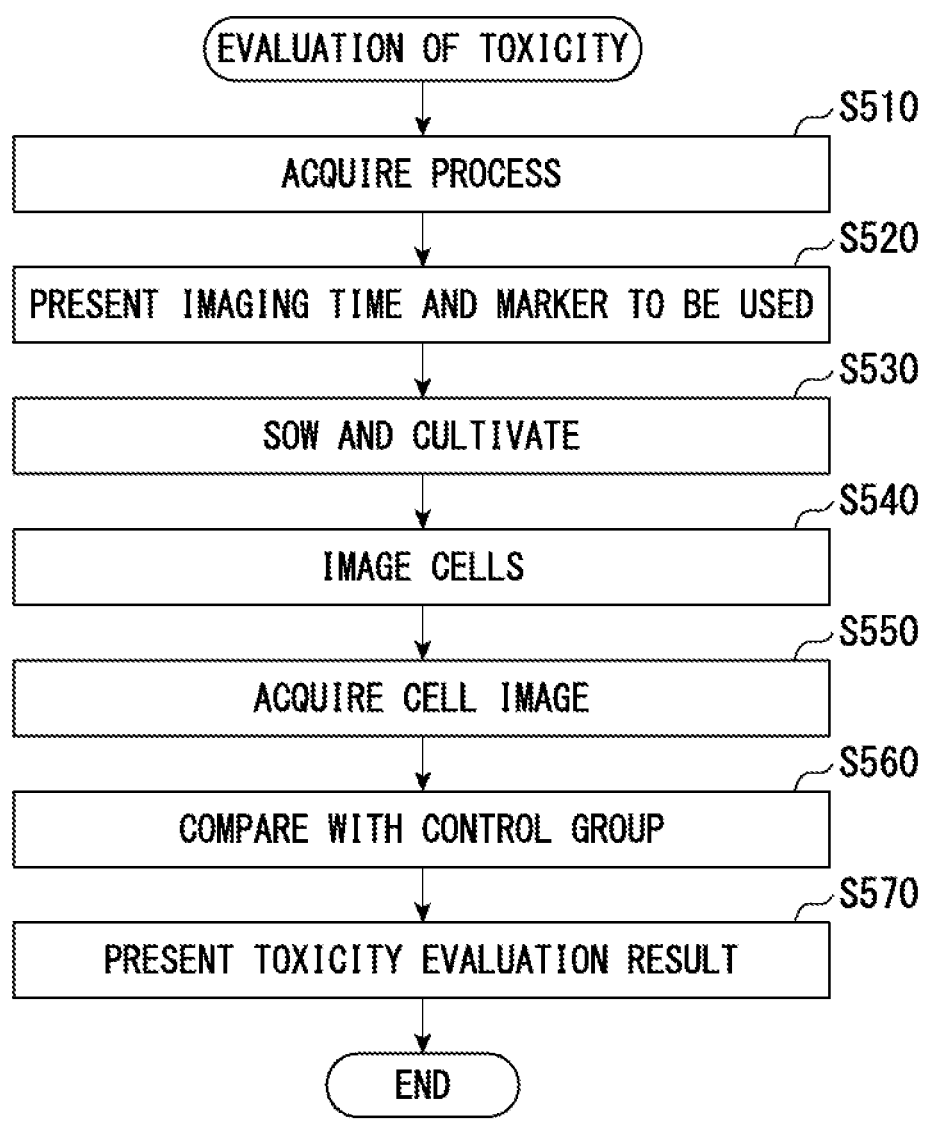
FIG. 14 is a diagram showing an example of a toxicity evaluation operation performed by the evaluation device of the present embodiment.

FIG. 14 is a diagram showing an example of an operation of evaluating toxicity performed by the evaluation device 10 of the present embodiment. In this example, the user of the evaluation device 10 inputs the Process which is an experiment target through the keyboard included in the operation detection unit 40. Each unit of the operation unit 100 acquires the Process input through the keyboard and detected by the operation detection unit 40 (step S510). The Process determination unit 120 acquires the Process and determines an imaging time according to the acquired Process. In addition, the marker selection unit 130 acquires the Process and selects a marker according to the acquired Process. The determined imaging time and the selected marker are displayed on the display unit 30 (step S520). The user dyes cells using the marker displayed in step S520. Dyeing may be manually performed by the user or automatically performed through a configuration including a dyeing device. The user sows cells as a comparison group of a control experiment in the wells W and starts cultivation (step S530). The imaging unit 22 of the microscope device 20 images each well W of the well plate WP at the imaging time determined in step S520 (step S540). The cell image extraction unit 110 extracts a cell image from images captured in step S540 (step S550). The toxicity evaluation unit 160 compares the extracted cell image as an experiment result with the experimental result with respect to the control group (step S560). The toxicity evaluation unit 160 generates a toxicity evaluation result on the basis of the comparison result in step S560 and outputs the generated evaluation result to the result output unit 300. The result output unit 300 displays the evaluation result through the display unit 30 (step S570).

Figure 15:
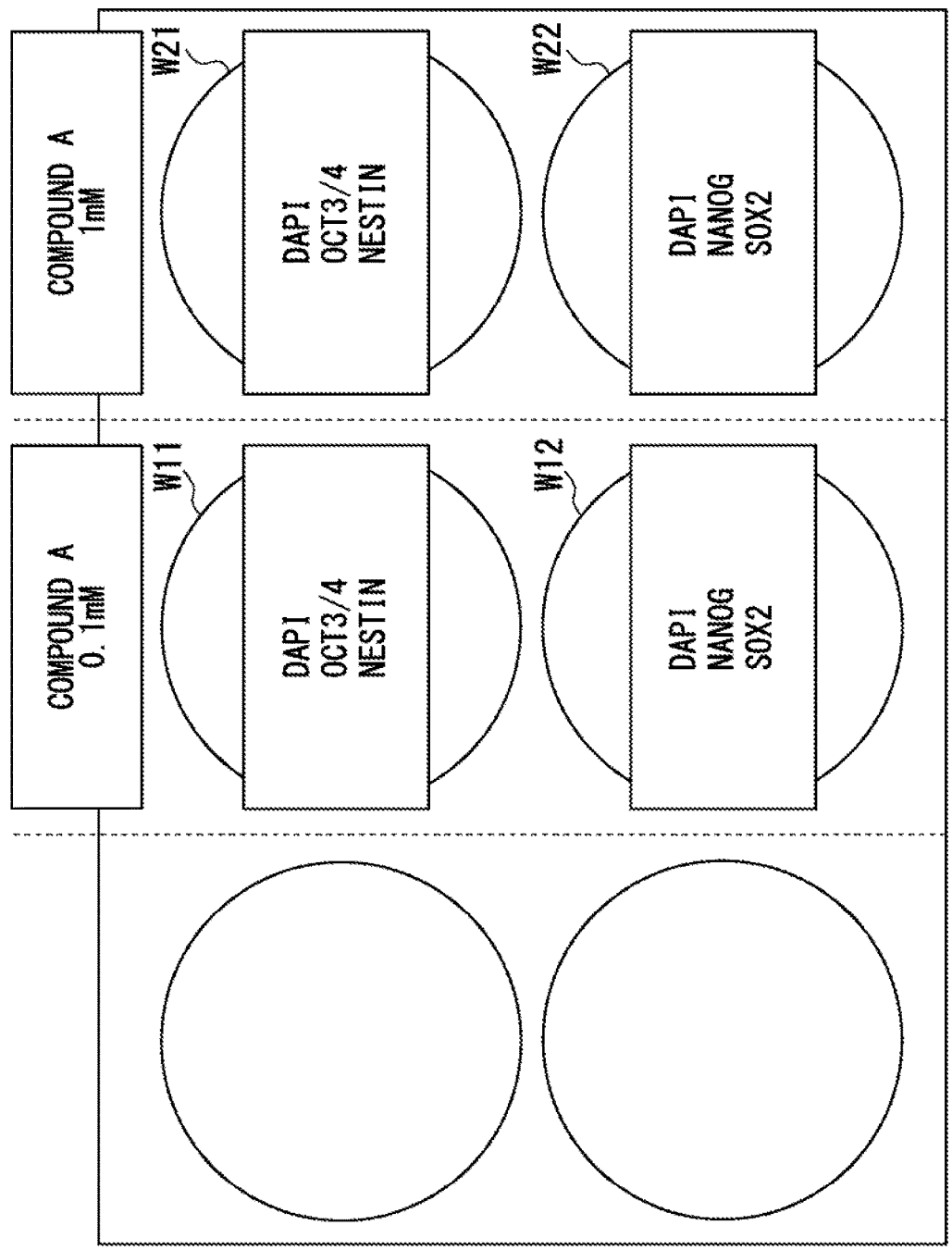
FIG. 15 is a diagram showing an example of a comparison group in a control experiment of the present embodiment.

Here, an example of the comparison group in step S530 is shown in FIG. 15.

FIG. 15 is a diagram showing an example of a comparison group in a control experiment of the present embodiment. The comparison group includes compounds A having different concentrations. Here, a compound A having a concentration of 0.1 [mM] is provided in a well W11 of the well plate WP. In addition, a compound A having a concentration of 1.0 [mM] is provided in a well W21 of the well plate WP.

In addition, results of comparison of experiment results obtained by the toxicity evaluation unit 160 will be described with reference to FIG. 16.

Figure 16:
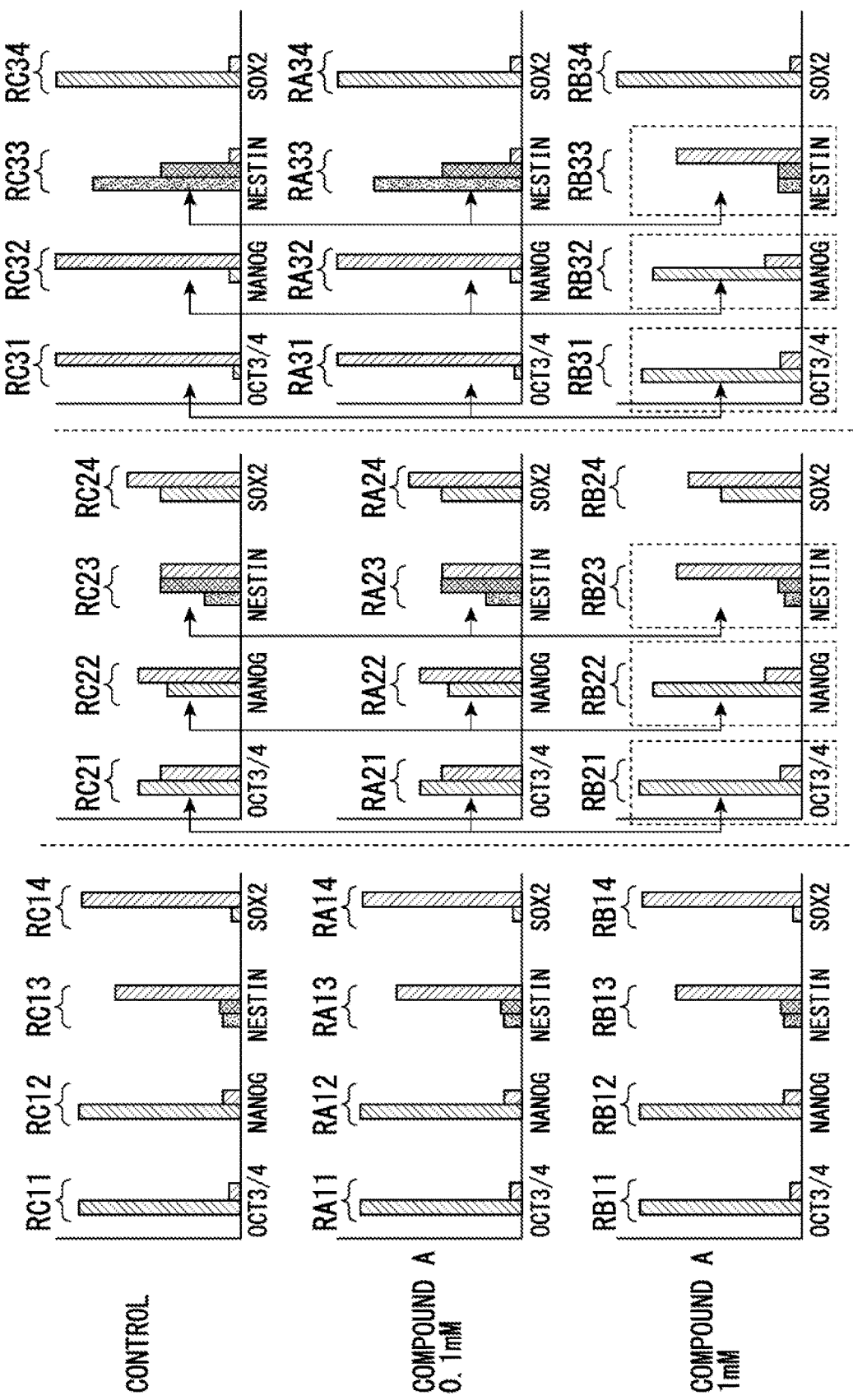
FIG. 16 is a diagram showing an example of comparison results of experimental results obtained by a toxicity evaluation unit of the present embodiment.

FIG. 16 is a diagram showing an example of results of comparison of experiment results obtained by the toxicity evaluation unit 160 of the present embodiment. The figure shows data of left groups, M central groups and right groups and represents experimental results at different timings in a differentiation process. The figure shows results when differentiation proceeds from the left groups to the right groups. The toxicity evaluation unit 160 acquires an experimental result with respect to a control group from the control group storage unit 240. In addition, the toxicity evaluation unit 160 acquires an experimental result with respect to a comparison group from the cell image extraction unit 110. Here, when the experimental results with respect to the control group and the comparison group are relatively close to each other, the toxicity evaluation unit 160 determines that the experimental result with respect to the comparison group is "toxicity is low." In addition, when the experimental results with respect to the control group and the comparison group are relatively distant from each other, the toxicity evaluation unit 160 determines that the experimental result with respect to the comparison group is "toxicity is high." In the example shown in FIG. 16, an experimental result RC11 with respect to the control group is similar to an experimental result RA11 with respect to the comparison group. Accordingly, the toxicity evaluation unit 160 determines that "toxicity is low" for compounds used for experiments of the experimental result RA11 and an experimental result RB11 with respect to the comparison group. In addition, an experimental result RC21 with respect to the control group is similar to an experimental result RA21 with respect to the comparison group. On the other hand, the experimental result RC21 with respect to the control group is not similar to an experimental result RB21. In this case, the toxicity evaluation unit 160 determines that "toxicity is low" for the compound used for the experiment of the experimental result RA21 with respect to the comparison group. Further, the toxicity evaluation unit 160 determines that "toxicity is high" for the compound used for the experiment of the experimental result RB21 with respect to the comparison group compared to the compound used for the experiment of the experimental result RA21 with respect to the comparison group. That is, the toxicity evaluation unit 160 determines that "toxicity is low" when a similarity between an experimental result with respect to the control group and an experimental result with respect to the comparison group is relatively high.

As described above, the evaluation device 10 of the present embodiment selects markers according to a cell differentiation process and presents the selected markers to the user of the evaluation device 10. Accordingly, the user is able to easily select a marker according to the cell differentiation process from markers of various types.

In addition, the evaluation device 10 of the present embodiment selects markers according to Process in which cells are differentiated, that is, a cell type of a differentiation origin and a cell type of a differentiation destination. Therefore, it is possible to present a marker suitable for evaluation of states before and after differentiation to the user of the evaluation device 10 according to the evaluation device 10. Accordingly, the user is able to easily select a marker according to states before and after differentiation from markers of various types.

Further, the evaluation device 10 of the present embodiment includes the experimental result storage unit which stores experimental results of cell differentiation under the standard conditions, that is, experimental results with respect to a control group. According to the evaluation device 10, it is possible to search the experimental result storage unit for experimental results with respect to the control group in control experiments. That is, according to the evaluation device 10, the user is able to easily obtain experimental results with respect to the control group when the user performs control experiments.

Moreover, the evaluation device 10 of the present invention includes the state determination unit which determines states of experimental results on the basis of experimental results with respect to a control group and experimental results with respect to a comparison group. According to the evaluation device 10, it is possible to determine experimental results without troubling the user.

In addition, the present application invention may employ a configuration including an observation condition determination unit which determines observation conditions for a cell which is an observation target under non-standard conditions on the basis of information acquired from cell images under standard conditions. In this case, the present application invention may not include the state determination unit which determines the state of a cell which is an observation target under the non-standard conditions on the basis of information acquired from cell images under the standard conditions.

Further, observation conditions for a cell which is an observation target under the non-standard conditions may be determined on the basis of information acquired from cell images under the standard conditions and the determined observation conditions may be corrected when it is determined that desired observation cannot be performed as a result of observation according to the observation conditions (e.g., determination from analysis of acquired images). For example, it may be possible to pay attention to a neurite generation timing and, when observation under the non-standard conditions at this timing is determined, to increase a predetermined observation time or newly set an observation timing if neurite generation has not occurred at the determined timing.

In addition, the evaluation device 10 of the present embodiment presents imaging conditions for cells. According to the evaluation device 10, it is possible to present imaging conditions in experiments of cell differentiation for a comparison group on the basis of imaging conditions during experiments of cell differentiations for a control group. That is, according to the evaluation device 10, the user is able to perform experiments on a comparison group according to the presented imaging conditions and thus imaging conditions for a control group and those for a comparison group can be made consistent.

Meanwhile, a case in which the markers of four types, "OCT3/4," "NANOG," "NESTIN" and "SOX2," are used for evaluation of a progress states of differentiation induction of cells has been described above as an example. Here, an example of Process of cell differentiation induction which is evaluated using markers such as "GalC (galactocerebroside)," "Tuj1 (tubulin antibody)" and "MAP2" will be further described.

Figure 17:
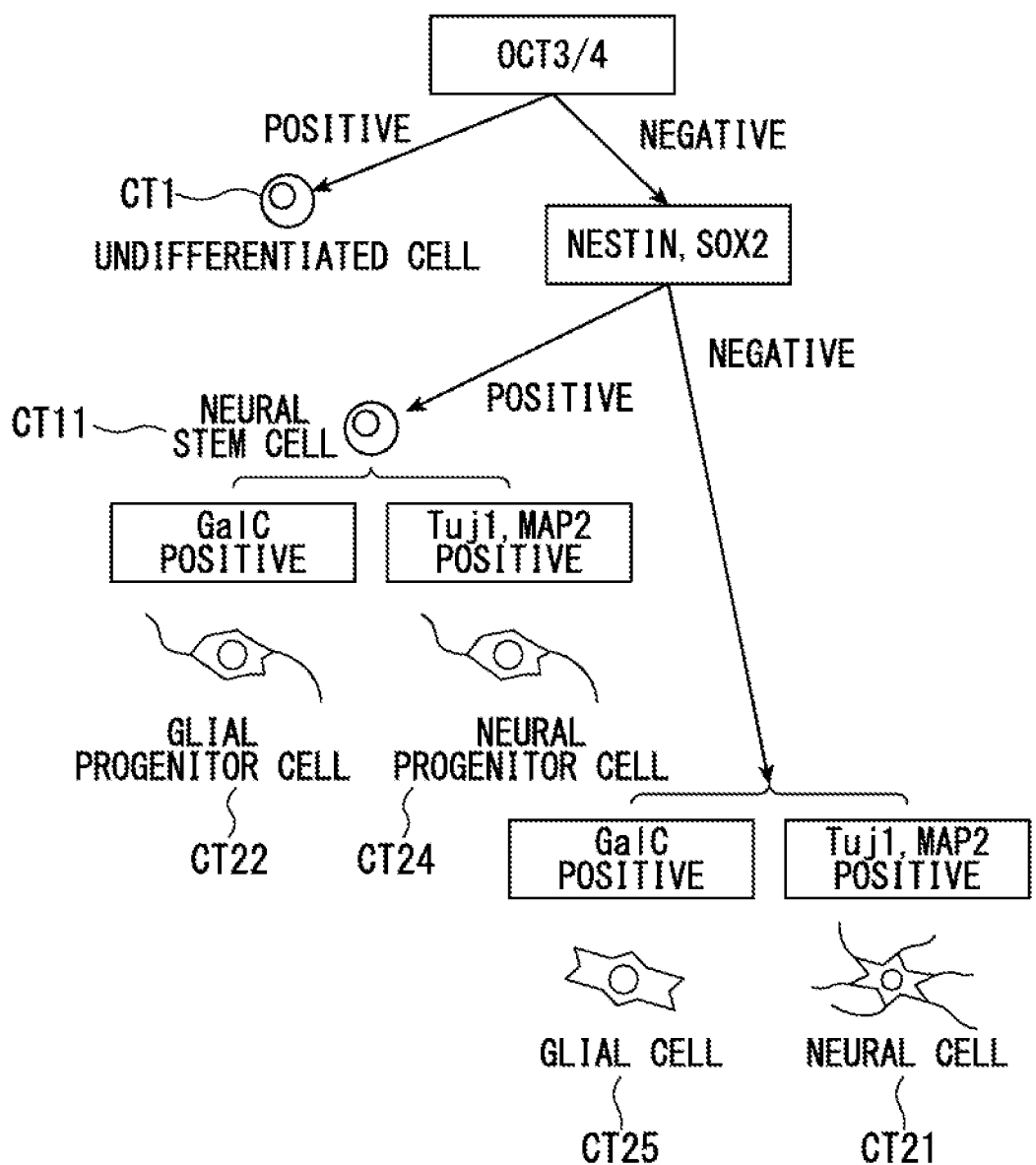
FIG. 17 is a diagram showing a first example of differentiation induction into neural cells of the present embodiment.

FIG. 17 is a diagram showing a first example of differentiation induction of a nervous system of the present embodiment. When expression of "OCT3/4" is positive with respect to certain cells, the cells are undifferentiated cells CT1. In addition, when expressions of "NESTIN" and "SOX2" are positive with respect to cells for which expression of "OCT3/4" is negative, there is a possibility that the cells are neural stem cells CT11. When expression of "OCT3/4" is positive with respect to cells which can be cells for which both expressions of NESTIN and SOX2 are positive, there is a possibility that the cells are the undifferentiated cells CT1.

If expression of "GalC" is positive with respect to cells for which both expressions of "NESTIN" and "SOX2" are positive, the corresponding cells are glial progenitor cells CT22. If both expressions of "Tuj1" and "MAP2" are positive with respect cells for which both expressions of "NESTIN" and "SOX2" are positive, the cells are neuronal precursor cells CT24.

If expression of "GalC" is positive with respect to cells for which both expressions of "NESTIN" and "SOX2" are negative, the cells are glial cells CT25. If both expression of "Tuj1" and "MAP2" are positive with respect to cells for which both expressions of "NESTIN" and "SOX2" are negative, the cells are neural cells CT21.

Figure 18:
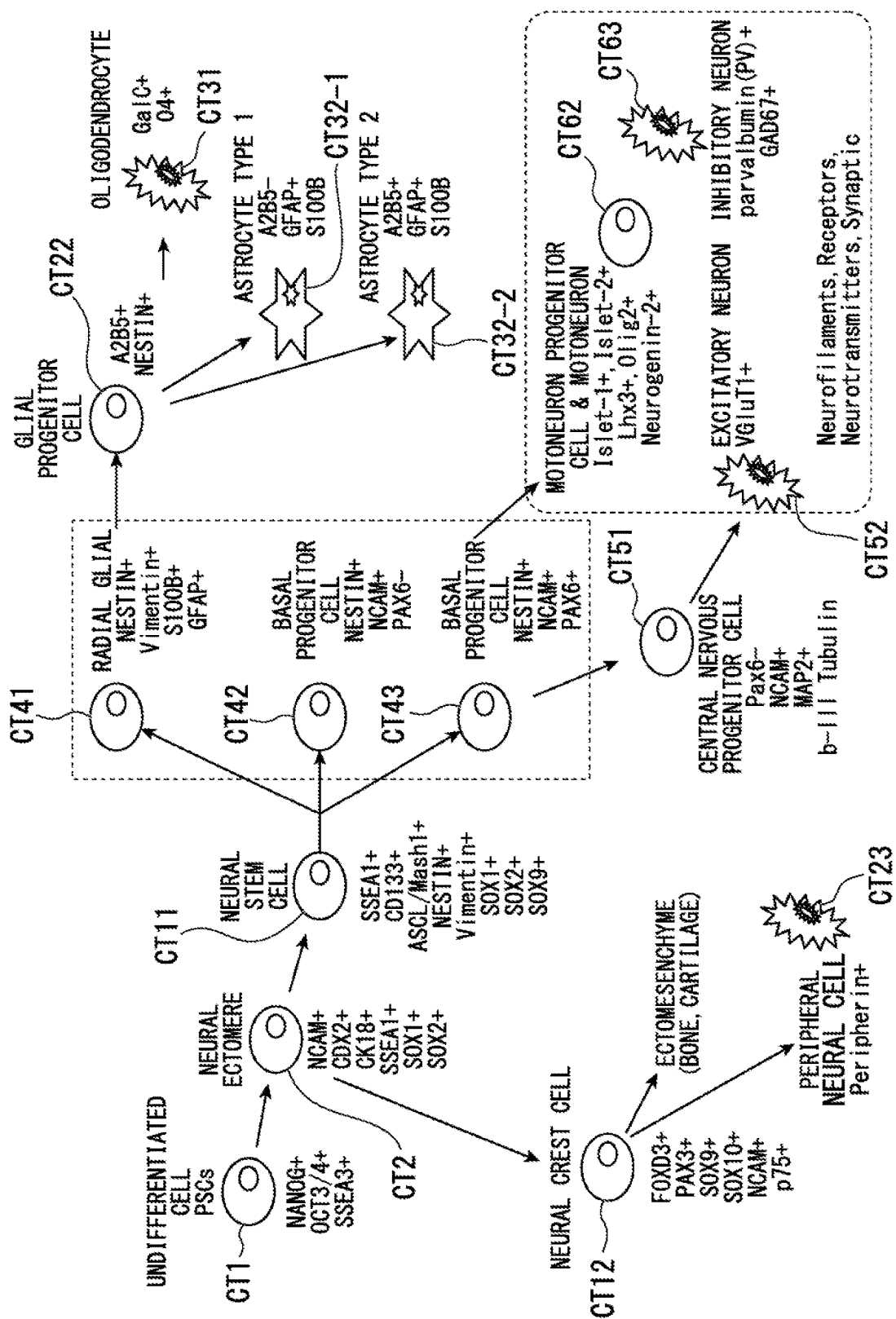
FIG. 18 is a diagram showing a second example of differentiation induction into neural cells of the present embodiment.

FIG. 18 is a diagram showing a second example of Process of differentiation induction of a nervous system of the present embodiment. In the case shown in FIG. 18, a progress state of differentiation induction of cells is also evaluated as in the case shown in FIG. 17. Meanwhile, + at the end of the name of each marker represents positivity and—represents negativity in FIG. 18. As shown in the figure, an evaluation of a degree of progress of differentiation induction of cells is facilitated using a combination of a plurality of markers, compared to cases in which a single marker is used.

Second Embodiment

Hereinafter, an observation device 2 in a second embodiment will be described. Meanwhile, the same components and operations as those of the above-described observation device 1 of the first embodiment are represented by the same signs and a description thereof is omitted.

Figure 19:
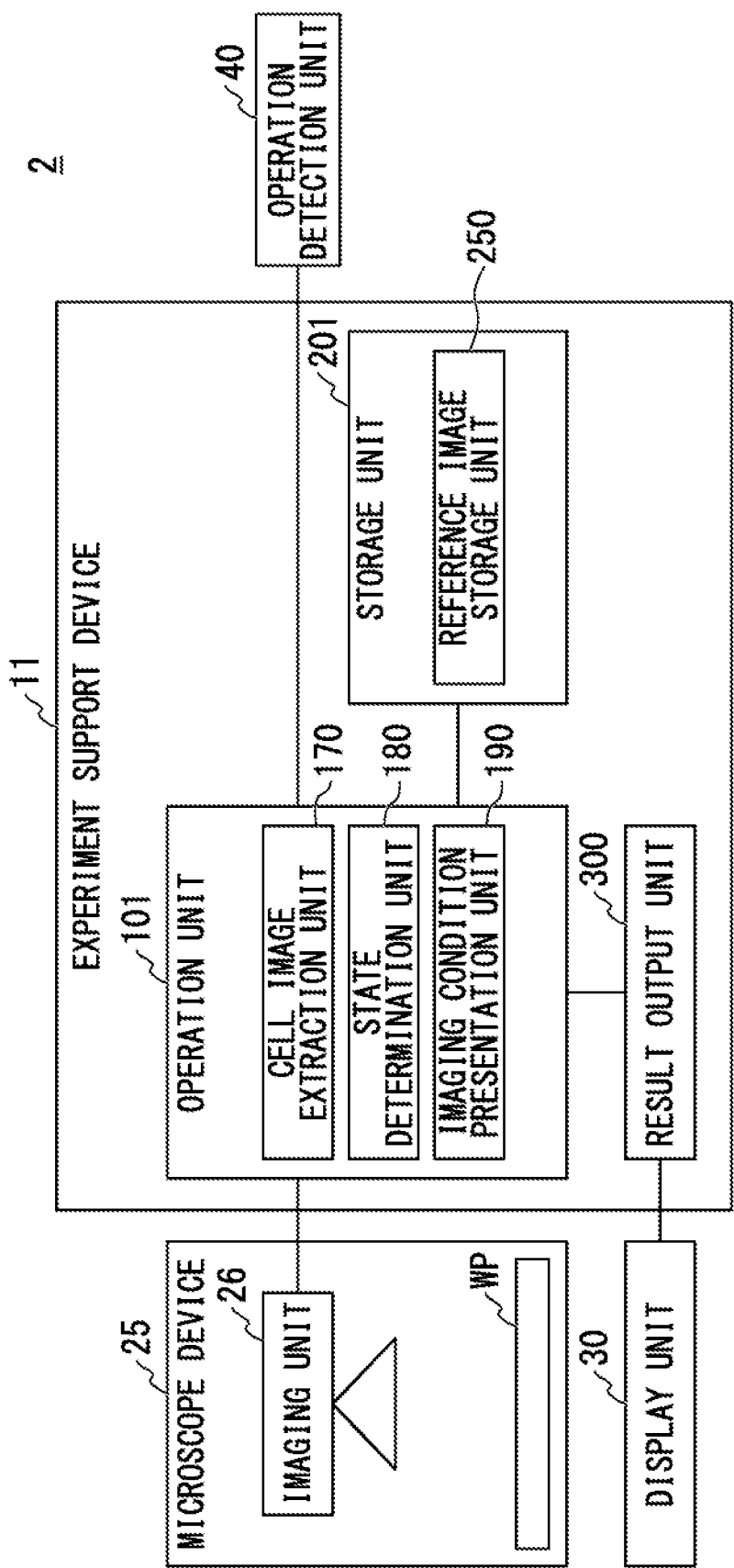
FIG. 19 is a block diagram showing a functional configuration of an evaluation device of a second embodiment.

FIG. 19 is a block diagram showing a functional configuration of an evaluation device 11 of the present embodiment. The observation device 2 includes the evaluation device 11 instead of the evaluation device 10. In addition, the observation device 2 includes a microscope device 25 instead of the microscope device 20. The aforementioned microscope device 20 captures fluorescent images of cells, whereas the microscope device 25 of the present embodiment captures images of the forms of cells. For example, the microscope device 25 is a phase-contrast microscope. The microscope device 25 includes an imaging unit 26. The imaging unit 26 captures images of the forms of cells to generate phase-contrast images. For example, the microscope device 25 is a time-lapse microscope. The imaging unit 26 captures images of the forms of cells with time in a cell differentiation process.

Images captured by the imaging unit 26 include a reference image and a differentiation process image. The reference image is an image obtained by a cell differentiation experiment under standard conditions. The differentiation process image is an image obtained by a cell differentiation experiment under control experiment conditions.

Here, the form of a cell includes the external shape of the cell, the number of neurites generated from the cell, the shape of the neurites, a shape distribution of the neurites, the size of the nucleus of the cell, the number of cells counted from the shape of the cell, and the like. The form of a cell changes with time in a cell differentiation process. For example, when a cell differentiation process proceeds, changes such as increase in the number of neurites and increase in a neurite length according to the progress of the cell differentiation process occur. Further, when a substance such as a compound is added to cells in process of differentiation, manners in which the forms of cells change may be different in a case in which the substance has been added and a case in which the substance has not been added. For example, when a substance such as a compound has been added to cells in process of differentiation, an increment of the number of neurites may be less than an increment of the number of neurites when the substance has not been added. In this manner, the influence of a substance on cells in process of differentiation may be determined by observing the forms of cells with time. Here, regarding the form of a certain cell in a differentiation process, it is possible to compare changes with time when a substance has not been added with changes with time when the substance has been added by capturing an image of the changes with time when the substance has not been added as a reference image. In this case, an experiment on cell differentiation under standard conditions is a cell cultivation experiment when no substance is added. In addition, the reference image is an image obtained by a cell differentiation experiment when no substance is added. Here, a cell differentiation experiment when no substance is added is also referred to as an experiment on a control group. That is, the reference image is an image obtained by an experiment on a control group.

The evaluation device 11 includes an operation unit 101, a storage unit 201 and a result output unit 300. The storage unit 201 includes a reference image storage unit 250.

The reference image storage unit 250 stores reference images captured by the imaging unit 26 under the aforementioned standard conditions.

Further, the reference image storage unit 250 may store information on the forms of cells extracted from the reference images in addition to or instead of the information of the reference images.

The operation unit 101 includes a cell image extraction unit 170, a state determination unit 180 and an imaging condition presentation unit 190 as functional units thereof.

The cell image extraction unit 170 extracts a cell image from images captured by the imaging unit 26. Description of a specific configuration is omitted because it is described in the first embodiment. The cell image extraction unit 170 provides the extracted cell image to each functional unit of the operation unit 101.

The state determination unit 180 determines a state of a process indicated by a differentiation process image on the basis of the aforementioned differentiation process image and information on the form of a cell indicated by the reference image. That is, the state determination unit 180 determines a state of a cell which is an observation target under non-standard conditions on the basis of information acquired from a cell image under the standard conditions.

The imaging condition presentation unit 190 presents conditions based on a time change in the form of a cell indicated by a plurality of reference images captured with time as imaging conditions for differentiation process images. For example, the imaging condition presentation unit 190 presents imaging conditions for reference images stored in the reference image storage unit 250 as imaging conditions for differential process images. Specifically, when reference images stored in the reference image storage unit 250 are images captured every day in a cell differentiation process, the imaging condition presentation unit 190 presents "every day" as imaging conditions for differentiation process images.

As described above, the evaluation device 11 of the present embodiment includes the state determination unit 180 which determines a state of an experimental result on the basis of experimental results with respect to a control group and experimental results with respect to a comparison group. According to the evaluation device 11, it is possible to determine experimental results without troubling the user.

In addition, the evaluation device 11 of the present embodiment presents imaging conditions for cells. According to the evaluation device 11, it is possible to present imaging conditions in cell differentiation experiments on a comparison group on the basis of imaging conditions during cell differentiation experiments on a control group, that is, imaging conditions for reference images. That is, according to the evaluation device 11, it is possible to make consistent imaging conditions for a control group and those for a comparison group because the user can perform experiments on the comparison group according to presented imaging conditions.

Meanwhile, the above-described various processes may be performed by recording a program for executing each process of the observation device 1 or the evaluation device 10 in an embodiment of the present invention in a computer-readable recording medium and causing a computer system to read and execute the program recorded in the recording medium.

Further, the "computer system" described here may include hardware such as an OS and a peripheral device. In addition, the "computer system" is regarded as also including a homepage provision environment (or display environment) if a WWW system is used. In addition, the "computer-readable recording medium" refers to a nonvolatile memory such as a flexible disk, a magneto-optic disk, a ROM or a flash memory, a portable medium such as a CD-ROM, and a storage device such as a hard disk embedded in a computer system.

Further, the "computer-readable recording medium" also includes a medium which stores programs for a certain time, such as a volatile memory (e.g., a dynamic random access memory (DRAM)) in a computer system which is a server or a client when the programs have been transmitted through a network such as the Internet or a communication line such as a telephone line. In addition, the aforementioned program may be transmitted from a computer system in which the program has been stored in a storage device or the like to other computer systems through a transmission medium or transmitted waves in the transmission medium. Here, the "transmission medium" through which programs are transmitted refers to a medium having a function of transmitting information, such as a network (communication network) such as the Internet and a communication channel (communication line) such as a telephone circuit. In addition, the aforementioned program may be a program for realizing some of the above-described functions. Further, the program may be so-called a differential file (differential program) which can be realized by combining the above-described functions with programs which have already been recorded in a computer system.

Although embodiments of the present invention have been described in detail with reference to the drawings, specific configurations are not limited to these embodiments and designs and the like within a range without departing from the spirit or scope of the present invention are also included. Although neural cells have been mainly described in the present embodiment, for example, the present invention is applicable to heart muscle cells, lever cells, iPS cells and the like, for example.

REFERENCE SIGNS LIST

1 Observation device
10 Evaluation device
100 Operation unit
110 Cell image extraction unit
120 Process determination unit
130 Marker selection unit
140 Control group registration unit
150 Marker change pattern extraction unit
160 Toxicity evaluation unit
230 Marker storage unit

What is claimed is:
1. An evaluation device comprising:
a processor;
a memory encoded with instructions executed by the processor, the instructions causing the processor to perform operations steps comprising:
  extracting an image of neural cells from images captured at more than one time point, wherein the extracted image comprises a differentiated state of the neural cells, and wherein the extracted image is identified using observation targets;
  selecting more than one marker, wherein each of the more than one marker is suitable for evaluating differentiated states of the neural cells and immunostaining to evaluate differentiated states of the neural cells, and each of the more than one marker representing a differentiation process of the neural cells corresponding to at least one of the observation targets;

storing, as a control experimental result, the extracted image of neural cells including a marker change pattern of the selected marker, wherein the extracted image is extracted after cultivation of a neural cell of a cell type that corresponds to the observation targets under a standard condition using a combination of the more than one selected markers, wherein the standard condition comprises a condition where a substance which potentially influences the neural cells in a process of differentiation induction has not been added to the neural cells;

comparing an experimental result based on the extracted image of neural cells with the control experimental result to determine a differentiated state of the neural cells which are observation targets after a cell cultivation under a non-standard condition using the combination of more than one selected markers selected for the neural cells, wherein the non-standard condition comprises a condition where the substance has been added to the neural cell; and wherein the differentiated state of the neural cells is determined based on the marker change pattern in expression state of the facilitated marker and the suppressed marker.

2. The evaluation device according to claim 1, wherein the instructions further cause the processor to perform operation steps comprising observing conditions for neural cells which are observation targets under the non-standard condition on the basis of information acquired from an image of neural cells under the standard condition.

3. The evaluation device according to claim 1, wherein the combination of the more than one selected markers includes a facilitated marker of induced expression corresponding to progress of differentiation induction of the neural cells and a suppressed marker of suppressed expression of progress of differentiation induction of the neural cells.

4. A non-transitory medium storing a program which, when executed on a computer, causes the computer to perform the following:
   an image acquisition step of acquiring a captured image of cells;
   an observation result acquisition step comprising acquiring an observation result of cells under a standard condition; and
   a cell image extraction step comprising extracting an image of neural cells from images captured at more than one time point, wherein the extracted image comprises a differentiated state of the neural cells, and wherein the extracted image is identified using observation targets;
   a marker selection step comprising selecting more than one marker, wherein each of the more than one marker is suitable for evaluating differentiated states of the neural cells and immunostaining to evaluate differentiated states of the neural cells, and each of the more than one marker representing a differentiation process of the neural cells corresponding to at least one of the observation targets; and
   storing, as a control experimental result, the extracted image of neural cells including a marker change pattern of the selected marker, wherein the cell image extraction step occurs after cell cultivation of a neural cell whose cell type is the same as the observation targets under a standard condition using a combination of more than one of the markers selected by the marker selection step, wherein the standard condition comprises a condition where a substance which potentially influences the neural cells in a process of differentiation induction has not been added to the neural cells;
   a state determination step of comparing an experimental result based on the extracted image of neural cells extracted with the control experimental result stored in the storage step to determine a differentiation state of the neural cells which are the observation targets after a cell cultivation under a non-standard condition using a combination of a plurality of the markers selected for the neural cells which are the observation targets in the marker selection step, wherein the non-standard condition comprises a condition where the substance has been added to the neural cell;
   wherein the combination of the more than one marker selected in the marker selection step includes a facilitated marker of which expression is facilitated with progress of differentiation induction of the neural cells and a suppressed marker of which expression is suppressed with the progress of differentiation induction of the neural cells,
   wherein the state determination step determines the differentiation state of the neural cells based on change of an expression states of the facilitated marker and the suppressed marker, and
   wherein the information on neural cells under the non-standard conditions is information on neural cells in process of differentiation induction under a condition where a substance which potentially influences the neural cells in process of induction differentiation has been added, and the information on neural cells under the standard conditions is information under a condition where the substance has not been added to the neural cells in process of differentiation.

5. The evaluation device according to claim 1, wherein the stored control experimental result is associated with an experimental result ID for each time of the progress of differentiation induction of the neural cells, the experimental result ID representing the marker change pattern.

6. The evaluation device according to claim 1, wherein the instructions further causing the processor to perform operations comprising evaluating toxicity of the substance under the non-standard condition on the basis of information on the marker change pattern of the marker extracted from the experimental result under the standard condition and information on the maker change pattern of the marker extracted from the experimental result under the non-standard condition.

7. The evaluation device according to claim 1, wherein the instructions further causing the processor to perform operations comprising:
   storing a plurality of the marker; and
   selecting a combination of the plurality of markers stored according to differentiation process of the neural cells.

8. The evaluation device according to claim 1, wherein the instructions further cause the processor to perform operations comprising:
   extracting a marker change pattern of a control group as information acquired from an image of neural cells under the standard conditions; and
   determining a differentiation state of the neural cells which are observation targets by comparing a marker change pattern of the neural cells which are observation targets with a marker change pattern of the control group.

9. The evaluation device according to claim 1, wherein the instructions further cause the processor to perform operations comprising:

storing a reference image obtained by capturing a differentiation process of the neural cells under a condition, as the standard conditions, where a substance which potentially influences a progress of differentiation induction of the neural cells has not been added;

presenting imaging conditions, based on a time change in the form of a neural cell indicated by the reference image, for a differentiation process image obtained by capturing a differentiation process of the neural cells under a condition, as the non-standard conditions, where the substance has been added; and determining information of a differentiation process indicated by the differentiation process image based on information on the form of a neural cell indicated by the differentiation process image and the reference image.

10. An observation device comprising the evaluation device of any one of claims 1, 2, or 3.

* * * * *